(12) United States Patent
van den Engh et al.

(10) Patent No.: US 7,679,039 B2
(45) Date of Patent: Mar. 16, 2010

(54) COMPOSITIONS AND METHODS FOR DROP BOUNDARY DETECTION AND RADIATION BEAM ALIGNMENT

(75) Inventors: Gerrit J. van den Engh, Seattle, WA (US); Peter I. Nelson, Fort Collins, CO (US)

(73) Assignee: The Institute for Systems Biology, Seattle, WA (US)

( * ) Notice: Subject to any disclaimer, the term of this patent is extended or adjusted under 35 U.S.C. 154(b) by 0 days.

(21) Appl. No.: 12/102,809

(22) Filed: Apr. 14, 2008

(65) Prior Publication Data
US 2008/0259342 A1    Oct. 23, 2008

Related U.S. Application Data

(63) Continuation of application No. 10/132,659, filed on Apr. 24, 2002, now Pat. No. 7,362,424.

(51) Int. Cl.
*G01J 1/36* (2006.01)
*G01N 21/17* (2006.01)

(52) U.S. Cl. .................. 250/204; 356/73; 356/614; 356/622

(58) Field of Classification Search ........... 356/121, 356/130–132, 139.01, 139.04–139.08, 141.1, 356/141.3, 614, 622; 250/203.1, 203.3, 203.4, 250/204, 206.1, 559.29
See application file for complete search history.

(56) References Cited

U.S. PATENT DOCUMENTS

| | | | |
|---|---|---|---|
| 2,612,814 A * | 10/1952 | Glasser ................ 356/132 |
| 2,740,901 A * | 4/1956 | Graham ................ 250/201.1 |
| 3,515,486 A * | 6/1970 | Vonderohe et al. ..... 356/139.07 |
| 3,654,475 A * | 4/1972 | Montpas ............... 250/203.6 |
| 3,813,172 A | 5/1974 | Walker et al. |
| 4,187,027 A | 2/1980 | Bjorklund et al. |
| 4,801,810 A | 1/1989 | Koso |
| 4,938,592 A | 7/1990 | Poole et al. |
| 4,993,796 A | 2/1991 | Kapany et al. |
| 5,602,039 A | 2/1997 | van den Engh |
| 5,608,526 A | 3/1997 | Piwonka-Corle et al. |

(Continued)

OTHER PUBLICATIONS

Asbury et al., "Polarization of Scatter and Fluorescence Signals in Flow Cytometry," *Cytometry*, 40:88-101 (2000).

(Continued)

*Primary Examiner*—F. L Evans
(74) *Attorney, Agent, or Firm*—McDermott Will & Emery, LLP

(57) ABSTRACT

The invention provides an apparatus and method for determining the position of a radiation beam. The apparatus includes (a) a first reflective surface and a second reflective surface, the reflective surfaces being placed to form the reflective exterior of a wedge; (b) a first detector placed to detect radiation reflected from the first reflective surface, and (c) a second detector placed to detect radiation reflected from the second reflective surface. The method includes the steps of (a) directing a radiation beam to the reflective exterior of a wedge formed by a first reflective surface and a second reflective surface; (b) selectively detecting radiation reflected from the first reflective surface; (c) selectively detecting radiation reflected from the second reflective surface; and (d) determining the position of the radiation beam based on the difference in the amount of radiation detected from each surface.

32 Claims, 17 Drawing Sheets

U.S. PATENT DOCUMENTS

| | | | |
|---|---|---|---|
| 5,819,948 | A | 10/1998 | van den Engh |
| 6,003,678 | A | 12/1999 | van den Engh |
| 6,034,763 | A | 3/2000 | Slater et al. |
| 6,067,157 | A | 5/2000 | Altendorf |
| 6,133,044 | A | 10/2000 | van den Engh |
| 6,353,657 | B1 | 3/2002 | Bayrock et al. |

OTHER PUBLICATIONS

Asbury et al., "Fluorescence Spectra of DNA Dyes Measured in a Flow Cytometer," *Cytometry*, 24:234-242 (1996).

Pinkel & Stovel, "Flow Chambers and Sample Handling," *Flow Cytometry: Instrumentation and Data Analysis*, London, Academic Press, pp. 77-127 (1985).

Shapiro, *Practical Flow Cytometry*, Wiley-Liss, New York, 1:1-31, 4:75-178, and 6:217-228 (1995).

van den Engh and Stokdijk, "Parallel Processing Data Acquisition System for Multilaser Flow Cytometry and Cell Sorting," Cytometry, 10:282 293 (1989).

van den Engh, G., "High Speed Cell Sorting," *Emerging Tools for Single-Cell Analysis*, Wiley-Liss, Inc., New York (2000).

International Society for Analytical Cytology: Letter of Acceptance and Registration Confirmation for Ger van den Engh, (letter signed Feb. 17, 2000).

\* cited by examiner

COMPOSITIONS AND METHODS FOR DROP BOUNDARY DETECTION AND RADIATION BEAM ALIGNMENT

This application is a continuation application of U.S. Ser. No. 10/132,659, filed Apr. 24, 2002, now U.S. Pat. No. 7,362,424, the entire contents of which are incorporated herein by reference.

This invention was made with government support under grant number DE-FG03-00ER63051 awarded by the United States Department of Defense. The United States Government has certain rights in this invention.

BACKGROUND OF THE INVENTION

This invention relates generally to separation of particles from mixtures and, more specifically, to flow cytometers for analyzing and sorting biological particles.

Flow cytometry is a valuable method for the analysis and isolation of biological particles such as cells and constituent molecules. As such it has a wide range of diagnostic and therapeutic applications. The method utilizes a fluid stream to linearly segregate particles such that they can pass, single file, through a detection apparatus. Individual cells can be distinguished according to their location in the fluid stream and the presence of detectable markers. Thus, a flow cytometer can be used to produce a diagnostic profile of a population of biological particles. For example, flow cytometry has been used to measure the decline or maintenance of immune cells during the course of treatment for HIV infection and to determine the presence or absence of tumor cells for prognosis and diagnosis of cancer patients.

Isolation of biological particles has been achieved by adding a sorting or collection capability to flow cytometers. Particles in a segregated stream, detected as having one or more desired characteristics, are individually isolated from the sample stream by mechanical or electrical removal. This method of flow sorting has been used to separate sperm bearing X and Y chromosomes for animal breeding, to sort chromosomes for genetic analysis, and to isolate particular organisms from complex biological populations.

A common flow sorting technique utilizes drop sorting in which a fluid stream containing linearly segregated particles is broken into drops and the drops containing particles of interest are electrically charged and deflected into a collection tube by passage through an electric field. Current drop sorting systems are capable of forming drops at a rate of 100,000 drops/second in a fluid stream that is passed through a nozzle having a diameter less than 100 micrometers. Drop sorting requires that the drops break off from the stream at a fixed distance from the nozzle tip. The distance is normally on the order of a few millimeters from the nozzle tip and can be maintained for an unperturbed fluid stream by oscillating the nozzle tip at a predefined frequency.

Typically, the linearly segregated particles in the stream are characterized as they pass through an observation point situated just below the nozzle tip. Once a particle is identified as meeting one or more desired criteria, the time at which it will reach the drop break-off point and break from the stream in a drop can be predicted. Ideally, a brief charge is applied to the fluid stream just before the drop containing the selected particle breaks from the stream and then grounded immediately after the drop breaks off. The drop to be sorted maintains an electrical charge as it breaks off from the fluid stream, and all other drops are left uncharged. The charged drop is deflected sideways from the downward trajectory of the other drops by an electrical field and collected in a sample tube. The uncharged drops fall directly into a drain.

Perturbations in a fluid stream, including turbulence caused by variability in the size of particles present in typical biological samples or drift in cytometer components can significantly impact the ability to predict which drop will contain a particle of interest. Improper prediction of which drop contains a particle can lead to loss of valuable particles which are often present in small amounts in biological samples. Even a brief lapse in the ability to accurately predict the contents of a drop can contaminate a fraction of desired particles with unwanted particles, thereby compromising the quality of the fraction or rendering it unfit for therapeutic administration.

Although diagnostic flow cytometers have been made available for common use in a variety of settings, flow sorting is more complicated and has been confined primarily to core facilities having dedicated operators. Currently flow sorters require relatively complicated setup and alignment procedures that often necessitate highly trained operators. While flow analyzers have seen many improvements towards ease of use due to automation and simplification, most of the improvements in flow sorters has been directed to increasing sort speed and the number of parameters used. The increases in speed and number of parameters has had the effect of increasing the complexity and precision required in flow sorters.

Thus, there exists a need for flow cytometers and cytometry methods that are capable of accurately isolating particles of interest. A need also exists for flow cytometers having sorting capability that can be used in typical lab settings without the need for dedicated operators. The present invention satisfies these needs and provides related advantages as well.

SUMMARY OF THE INVENTION

The invention provides an apparatus for determining the position of a radiation beam. The apparatus includes (a) a first reflective surface and a second reflective surface, the reflective surfaces being placed to form the reflective exterior of a wedge; (b) a first detector placed to detect radiation reflected from the first reflective surface, and (c) a second detector placed to detect radiation reflected from the second reflective surface, wherein the first and second detectors are placed to selectively detect radiation reflected from different surfaces of the wedge. Also provided is a method for determining the position of a radiation beam. The method can include the steps of (a) directing a radiation beam to the reflective exterior of a wedge formed by a first reflective surface and a second reflective surface; (b) selectively detecting radiation reflected from the first reflective surface; (c) selectively detecting radiation reflected from the second reflective surface; and (d) determining the position of the radiation beam based on the difference in the amount of radiation detected from each surface.

DETAILED DESCRIPTION OF THE INVENTION

This invention provides apparatus for determining the position of a radiation beam. An apparatus of the invention includes reflective surfaces placed to form a wedge such that radiation contacting the wedge is directed to different detectors. The position of the radiation beam can be determined from the difference in the amount of radiation contacting each detector. An apparatus of the invention can be used to determine the position of a radiation beam relative to a fluid stream. Thus, methods for determining position of a radiation beam and aligning a radiation beam with respect to a fluid stream are provided. The methods and apparatus of the invention can be particularly useful in aligning the fluidic and optical pathways of a flow cytometer or flow sorter.

An apparatus of the invention can also be used to determine dynamics of a fluid stream according to changes detected in the properties of radiation following contact with the fluid stream. In particular, oscillations in a fluid stream can be monitored from oscillations in the amount of radiation contacting each detector. Accordingly, the invention provides methods for monitoring the dynamics, such as oscillation characteristics, of a fluid stream. The invention also provides methods for determining a drop boundary or drop break-off point based on oscillation characteristics of a fluid stream. Further provided by the invention are apparatus and methods for monitoring the quality of drop formation or locating drops containing a particle of interest in a flow sorter. An advantage of the invention is that drop formation can be monitored in real time such that the drop in which a particle will reside and disruptions in drop formation can be predicted before drops are formed and sorting decisions are made. Thus, the methods and apparatus of the invention can be used to increase sort yield while insuring high sort purity.

The invention further provides automated methods for aligning a radiation beam, halting or continuing sorting based on the quality of drop formation in an oscillating fluid stream, or identifying a drop containing a particle of interest for isolation or sorting. An advantage of the automated methods of the invention is that they can provide rapid responses to the dynamics of a fluid stream, or changes therein, for real time alignment of flow sorter components and real time drop sorting decisions.

As used herein, the term "wedge" is intended to mean an orientation of surfaces where the surfaces are angled toward each other such that the distance separating the surfaces is less at one end compared to the other. The term can include two surfaces that contact each other at the closer of two ends forming a ridge at the point of contact. The term can include surfaces that are planar. Surfaces of any shape can be used so long as the surfaces, when placed in a wedge, reflect a radiation beam outward to one or more detectors such that the position of the radiation beam can be determined.

Figure 1:
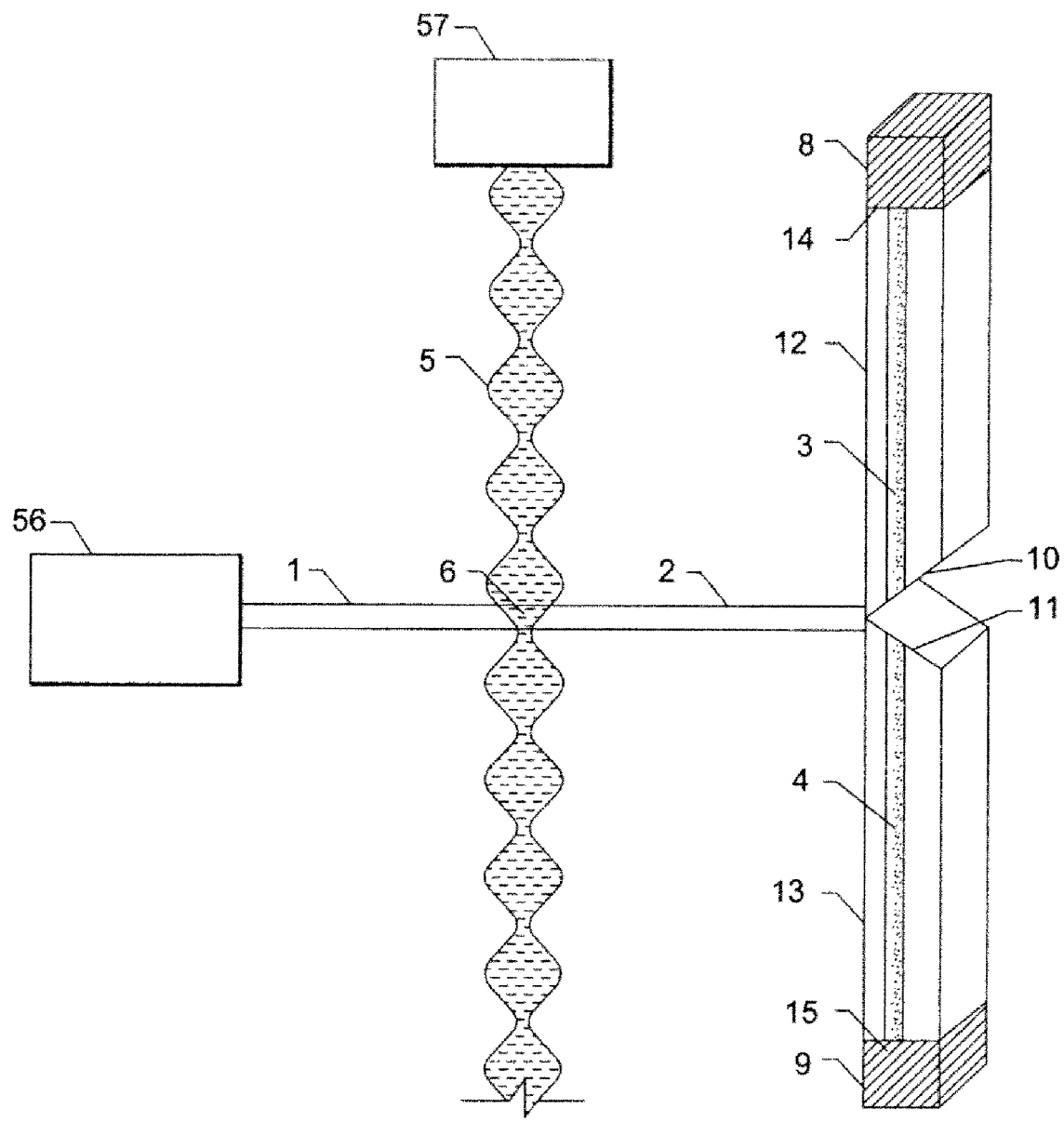
FIG. 1 shows a photodiode difference detector having two photodiode detectors.

As used herein the term "exterior," when used in reference to a wedge, is intended to mean a side of the wedge that faces outward. The side of the wedge that faces outward can be the interior surface of a surrounding material. For example, a wedge formed by two beveled glass surfaces can have an exterior that is formed by the reflective interior surfaces of the glass surrounding the wedge as shown in FIG. 1. The reflective side of the wedge that faces outward can also include the reflective outer surface of two mirrors.

As used herein, the term "reflective," when used in reference to a surface is intended to mean a surface that is able to redirect a radiation beam in the UV, VIS or IR regions of the spectrum such that the angle of incidence is equal to the angle of reflection where the incident beam, reflected beam, and normal to the beams are coplanar. The term can include, for example, an internal surface of a transparent material such as a surface of a prism, a surface formed at the interface of two materials such as metal coated glass or metal coated quartz or the exterior surface of a polished material such metal or plastic. Examples of metals that can form a mirror when coated on glass or quartz or when polished include aluminum, silver, platinum or gold.

As used herein, the term "detector" is intended to mean a device or apparatus that converts the energy of contacted photons into an electrical response. The term can include an apparatus that produces an electric current in response to impinging photons such as in a photodiode or photomultiplier tube. A detector can also accumulate charge in response to impinging photons and can include, for example, a charge coupled device.

As used herein, the term "oscillating," when used in reference to a fluid stream, refers to periodic changes of the diameter of the fluid stream or periodic disturbances of the surface of the fluid stream. The term can include changes or disturbances that are caused by acoustic waves or pressure variations that are coupled to the fluid stream.

As used herein the term "drop break-off point" refers to the location in the path of a fluid stream where fluid fragments separate from the stream. The location can be identified as a distance from a point in the stream including, for example, a distance from a nozzle or from a point of detection upstream of the location where drops separate from the stream.

As used herein the term "drop boundary" refers to a location in an oscillating fluid stream where the diameter of the stream is narrowed. The term can include any narrowed region in a fluid stream so long as the narrowed region decreases in diameter downstream and becomes a point of separation of a liquid fragment from the stream.

As used herein the term "selectively detect," when used in reference to a first and second reflective surface, is intended to mean observing reflected radiation such that a difference in the amount or quality of radiation propagating from the first surface can be differentiated from the amount or quality of radiation propagating from the second surface. When used in reference to points or locations on a reflective surface the term is intended to mean observing reflected radiation such that a difference in the amount or quality of radiation propagating from a first point or location on the surface can be differentiated from the amount or quality of radiation propagating from a second point or location on the surface. The term can include, for example, observation by separate detectors or with a detector that is capable of differentiating the amount or quality of radiation that contacts different locations on the detector. Such differentiation can be spatial, where different locations are observed simultaneously by one or more detector or temporal where different locations are observed at different times by the same detector.

As used herein, the term "pinhole mirror" is intended to mean a radiation screen having a surface that is sufficiently smooth to produce an image by specular reflection and a cavity that extends through a screen such that radiation in the UV, VIS or IR regions of the spectrum can pass. Specular reflection occurs when parallel rays of incident radiation, reflected according to the laws of reflection, are reflected parallel to each other at a surface. The laws of reflection hold that the angle of incidence is equal to the angle of reflection and the incident ray, reflected ray, and normal to the rays are coplanar. Diffuse reflection occurs when parallel incident rays are not parallel when reflected at a surface according to the laws of reflection, for example, due to irregularity in the surface. The term includes a cavity having, for example, a width, diameter or major axis of about 1.5 mm or less, 1.2 mm or less, 1.0 mm or less, 0.8 mm or less, 0.6 mm or less, 0.4 mm or less, 0.2 mm or less, or 0.1 mm or less. The term is intended to include a cavity containing any material transparent to irradiation in the UV, VIS or IR regions of the spectrum including, for example, air, glass, or quartz. Thus, a pinhole mirror can be a transparent substrate having a metallic coating where the coating contains a hole and the hole does not pass through the transparent substrate. A cavity can contain a material that is selectively transparent to irradiation of a particular wavelength or wavelengths such as a filter material. A cavity included in the term can have any cross sectional shape including, for example, circular, elliptical, or square and can have uniform or non-uniform cross sectional dimensions along the axis that runs through the center of the cavity from the front to the back of the screen material. An example, of a cavity with uniform cross sectional dimensions along the axis that runs through the center of the cavity is a cylindrical pin hole. Alternatively, a cavity can have non-uniform cross sectional dimensions along the axis that runs through the cavity such as that of a conical cavity.

As used herein, the term "radiation beam" is intended to refer to a collection of electromagnetic waves or particles propagated in a uniform direction of propagation. The term is intended to include detectable collections of waves or particles having any energy in the electromagnetic spectrum. Examples of detectable collections of waves or particles include ultra violet (UV) radiation in the range of about 200 to 390 nm, visible (VIS) radiation in the range of about 390 to 770 nm, and infrared (IR) radiation in the range of about 0.77 to 25 microns.

The invention provides an apparatus for determining the position of a radiation beam. The apparatus includes (a) a first reflective surface and a second reflective surface, the reflective surfaces being placed to form the reflective exterior of a wedge; (b) a first detector placed to detect radiation reflected from the first reflective surface, and (c) a second detector placed to detect radiation reflected from the second reflective surface, wherein the first and second detectors are placed to selectively detect radiation reflected from different surfaces of the wedge. The apparatus is referred to herein as a difference detector.

A difference detector of the invention can be used in a method to determine the position of a radiation beam. The method can include the steps of (a) directing a radiation beam to the reflective exterior of a wedge formed by a first reflective surface and a second reflective surface; (b) selectively detecting radiation reflected from the first reflective surface; (c) selectively detecting radiation reflected from the second reflective surface; and (d) determining the position of the radiation beam based on the difference in the amount of radiation detected from each surface.

An example of a difference detector of the invention is shown in FIG. 1. A reflective wedge is formed by abutting the beveled surfaces 10 and 11 on two ¹⁄₁₀ inch thick glass microscope slides 12 and 13. Beveled surfaces 10 and 11 of glass slides 12 and 13 are at a 45 degree angle such that when abutted they form a 90 degree angle between each other. Glass slides 12 and 13 are 0.59 inch in length and have a flat end 14 and 15, respectively, opposite the beveled ends 10 and 11. Beveled ends 10 and 11 and flat ends 14 and 15 of the slide are polished. The ends were polished on a lapping wheel using a series of diamond grit wheels. Mounted to each slide at flat ends 14 and 15 by a machined housing is a ¼ inch diameter photodiode 8 and 9, respectively (A-453; Melles Griot, Irvine, Calif.).

A radiation beam 1, from a radiation source 56, optionally contacts a particle 6 in a fluid stream 5 exiting from an optionally positionally adjustable nozzle 57. For simplicity, radiation scattered by particle 6 is not shown in FIG. 1 and the only radiation shown leaving the fluid stream is direct radiation beam 2 which contacts the wedge formed by surfaces 10 and 11. Radiation that contacts surface is reflected through glass slide 12, through flat end 14 and to photodiode 8, the path of which is shown by beam 3. Similarly, radiation that contacts 10 surface 11 is reflected in the opposite direction through glass slide 13, through flat end 15 and to photodiode 9, the path of which is shown by beam 4. When beam 2 is centered on the wedge, the amount of radiation directed to photodiode 8 is equivalent to the amount of radiation directed to photodiode 9 and the detectors are balanced with a difference output of 0 volts. Changes in the position of beam 2 can be detected according to the amplitude and sign of the difference output of photodiodes 8 and 9. For example, in the orientation shown in FIG. 1, a change in the position of radiation beam 2 in the upward direction will cause an increased output of photodiode 8 relative to photodiode 9. As the beam is moved upward from the centered position, a larger proportion of the radiation contacting the wedge is reflected to photodiode 8 and the output of photodiode 8 increases, thereby causing an increase in the amplitude of the difference output. Alternatively, if the beam is moved downward from the centered position the amplitude of the difference output also increases but with the opposite sign (positive or negative).

Because the position of the radiation beam can be determined from the sign and amplitude of the difference detector output, the difference detector can be used in a method to align the radiation beam. Furthermore, as set forth below in further detail, when radiation contacting the wedge has passed through a fluid stream, the output of the difference detector can be correlated with properties of a fluid stream. Thus, the output of the difference detector can be used to detect a change in the diameter of a fluid stream or to monitor oscillations in the diameter of a fluid stream.

As shown by the difference detector exemplified in FIG. 1, a reflective surface can be an inner surface of a transparent material. The reflective surfaces of a wedge of the invention can be those of one or more transparent members. As shown in FIG. 1, two transparent members having beveled ends can be abutted at their points to form a wedge. Alternatively, an apparatus of the invention can include a single transparent member having a wedge shaped cutout. Multiple members can be placed to form a wedge having two or more reflective surfaces as set forth below in more detail.

A transparent member used in the invention can be selected from any material or combination of materials that can pass radiation of a wavelength to be detected. Examples of useful materials include glass, plastic or quartz. A material can be selected based on its known transmittance properties. For example, because glass is opaque to certain wavelengths of UV radiation it can be used in application where transmittance of radiation having these wavelengths is undesirable. Alternatively, quartz or some plastics can be used if transmittance of UV light having wavelengths below the cutoff for glass is desired. A material can be chosen for its ability to transmit radiation of any wavelength or range of wavelengths in the UV, VIS, or IR regions or in any combination of these ranges. Thus, the material can be an optical filter such as colored glass. A material can be machined, molded, cut or polished using well known methods in order to produce a reflective surface or wedge used in the invention.

A reflective surface used in the invention can be an exterior surface such as a mirrored surface. Any reflective surface formed at the interface of two materials such as metal coated glass or metal coated quartz or the exterior surface of a polished material such metal or plastic can be included as reflective surfaces of a wedge of the invention. Examples of metals that can form a mirror when coated on glass or quartz or when polished include aluminum, silver, platinum or gold.

A reflective surface used in a wedge of the invention can act as an optical filter that selectively passes or reflects radiation in a wavelength, polarization or frequency dependent manner. An example of a filter that can be used in a wedge is an interference filter in which multiple layers of dielectric materials pass or reflect radiation according to constructive or destructive interference between reflections from the various layers. Interference filters are also referred to in the art as dichroic filters, or dielectric filters. Such filters can be used to reflect radiation having a desired wavelength to a detector while allowing passage of radiation having different wavelengths.

A wedge of the invention can have multiple surfaces placed to direct a radiation beam in multiple directions. For example, four surfaces can be placed to form a pyramid shaped wedge that reflects a radiation beam in four directions when the beam is centered at the apex. Increasing numbers of surfaces can be accommodated upwards to an infinite number of surfaces forming a cone. Detectors can be placed symmetrically around an arc to detect radiation reflected from locations around the apex formed by multiple reflective surfaces.

A difference detector of the invention can include any detector capable of detecting radiation reflected from the exterior of a wedge. Any of a variety of radiation detectors that are known in the art can be used in the methods including, for example, a photomultiplier tube, photodiode or camera. An appropriate detector can be selected based on the known properties of the detector such as wavelength sensitivity range and the wavelength of the radiation beam directed to the difference detector.

A detector can be attached to one or more transparent members having a reflective inner surface as shown, for example, in FIG. 1. A detector can also be unattached to the transparent members or the reflective surfaces of the wedge. A detector can be placed to directly observe a reflective surface of a wedge. Alternatively, intervening reflective surfaces can be included to direct radiation from a reflective surface of the wedge to the detector. Thus, detectors used in the invention can be placed in a variety of orientation to accommodate a particular application or particular constraints of an instrument in which it is used such as space constraints or desired placement of component parts.

The placement and relative locations of the component parts of the difference detector of the invention can be altered from those described by example above and exemplified in FIG. 1, so long as the difference detector is capable of determining the position of a radiation beam. For example, although the angle separating the reflective surfaces of the wedge shown in FIG. 1 is 90 degrees, this angle can be any angle greater than 0 degrees and less than 180 degrees so long as radiation directed from each surface can be selectively detected and correlated with the position of the radiation beam. Angles less than 90 degrees that can be used include, for example, angles of 85, 80, 70, 60, 50 or 45 degrees or less. The surfaces can be separated by angles less than 90 degrees to allow an increase in the angle at which a beam contacting the wedge is reflected compared to the angle of reflection from a beam propagating in the same direction toward a wedge having reflective surfaces separated by 90 degrees. A wedge can also have reflective surfaces separated by an angle greater than 90 degrees such as angles of 95, 100, 110, 120, 130 or 135 degrees which will allow a decrease in the angle at which a beam contacting the wedge is reflected compared to the angle of reflection from a beam propagating in the same direction toward a wedge having reflective surfaces separated by 90 degrees. Changing the angle of reflection from the surfaces of a wedge from the angles produced by a 90 degree wedge can provide for alternative placement of components to accommodate a particular instrument's space constraints.

The difference detector shown in FIG. 1 is oriented with radiation beam 2 directed in line with the line bisecting the angle separating reflective surfaces 10 and 11. The difference detector can be used to determine a change in the position of radiation beam 2, where the change causes the radiation beam to move upward or downward in position while propagating in a direction parallel to its original position. A change in the direction of propagation for radiation beam 2, where the radiation beam is out of line with the line bisecting the angle separating reflective surfaces 10 and 11, can also be determined by the difference detector so long as the change in position of the beam alters the amount of radiation directed to each detector. Thus, a difference detector can be used to observe changes in the position of a radiation beam due to translation or tilt of the beam.

The invention can be used to align a radiation beam produced by a variety of sources known in the art including, for example, a lamp such as an arc lamp or quartz halogen lamp, or a laser. Lasers useful in the invention include, for example, an ion laser such as argon ion or krypton ion laser, helium neon laser, helium cadmium laser, dye laser such as a rhodamine 6G laser, YAG laser or diode laser. These and other lasers useful in the invention are known in the art as described, for example, in Shapiro, *Practical Flow Cytometry*, $3^{rd}$ Ed. Wiley-Liss, New York (1995). If desired, radiation can be directed or focused using well known optical devices such as lenses, prisms or mirrors. A radiation source to be used in the invention can be chosen to suit a particular application or to be compatible with other components of the apparatus such as the transmittance properties of transparent members or the wavelength detection range of detectors.

An apparatus of the invention can further include a differential amplifier that compares the intensity of radiation detected at a first and second detector. A differential amplifier can be used to produce a signal having an amplitude and sign that correlates with the differences in the output of a first detector and second detector. Thus, when the first and second detector are placed to selectively detect radiation reflected from a wedge formed by a first and second reflective surface, respectively, the output of the differential amplifier will correlate with the position of a radiation beam contacting the wedge. The position of the radiation beam indicated by the output of the differential amplifier can be used to guide repositioning of the beam whether manual or automated. Furthermore, as set forth below in further detail, when radiation contacting the wedge has passed through a fluid stream, the output of the differential amplifier can be correlated with properties of a fluid stream. Thus, the output of the differential amplifier can be used to detect a change in the diameter of a fluid stream or to monitor oscillations in the diameter of a fluid stream.

A difference detector of the invention can further include a third reflective surface placed to reflect radiation to the surface of a wedge formed by a first and second reflective surface. The third reflective surface can be any of a variety of reflective surfaces known in the art including, for example, those described above in regard to the first and second reflective surfaces of a wedge. An example of such a reflective surface is the piezo mounted mirror shown in FIG. 4. The piezo mounted mirror 20 is placed in the optical path of an excitation radiation beam such that it directs the beam through a fluid stream and to the wedge formed by reflective surfaces 10 and 11. The piezo mounted mirror 20 can consist of a one inch mirror (02-MPG-007; Melles Griot, Irvine, Calif.) mounted, using a UV-polymerizable glue, on four piezoelectric stacks (AE0203D08; Thorlabs, Newton, N.J.) placed 90 degrees apart around the rim of the mirror.

Figure 4A:
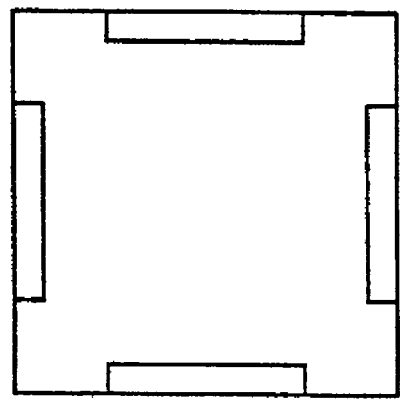
FIG. 4 shows a piezo mounted mirror of the invention.
Figure 4B:
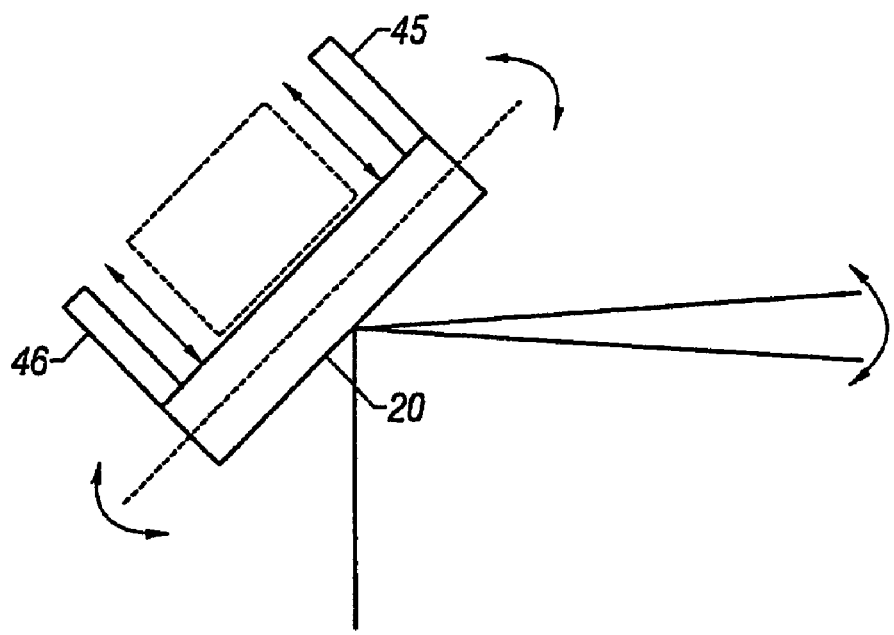

Thus, the invention provides a reflective surface attached to a positioning device. Movement of the reflective surface by means of the positioning device can provide the capability of changing the position of the radiation beam. Such movement can be used to align the radiation beam with the reflective surface of the wedge of the difference detector. FIG. 4 shows two of the piezoelectric stacks 45 and 46. The piezoelectric elements are powered by piezoelectric controllers 43 and 44, respectively (MDT690; Thorlabs, Newton, N.J.), that produce voltages from 0 to 100 volts. The piezoelectric elements can be operated in pairs, one pair aligned horizontally such that changes in the length of the piezo stacks cause the mirror to tilt horizontally, and the other pair aligned vertically such that changes in the length of the piezo stacks cause the mirror to tilt vertically. The combined changes in length for all four stacks can be used to rotate the mirror.

The position of a radiation beam to be aligned using an apparatus or method of the invention can be changed in response to the output of a difference detector either manually or by an automated device or process. The position of a radiation beam can be changed by altering the position of the radiation source or by altering the position of optical components in the path from the radiation source to the difference detector. The position of the radiation source or optical component can be altered in response to the output of a difference detector using a feed back circuit. An automated method for aligning a radiation beam using the output of a difference detector and a feedback circuit is described in Example I.

Figure 5:
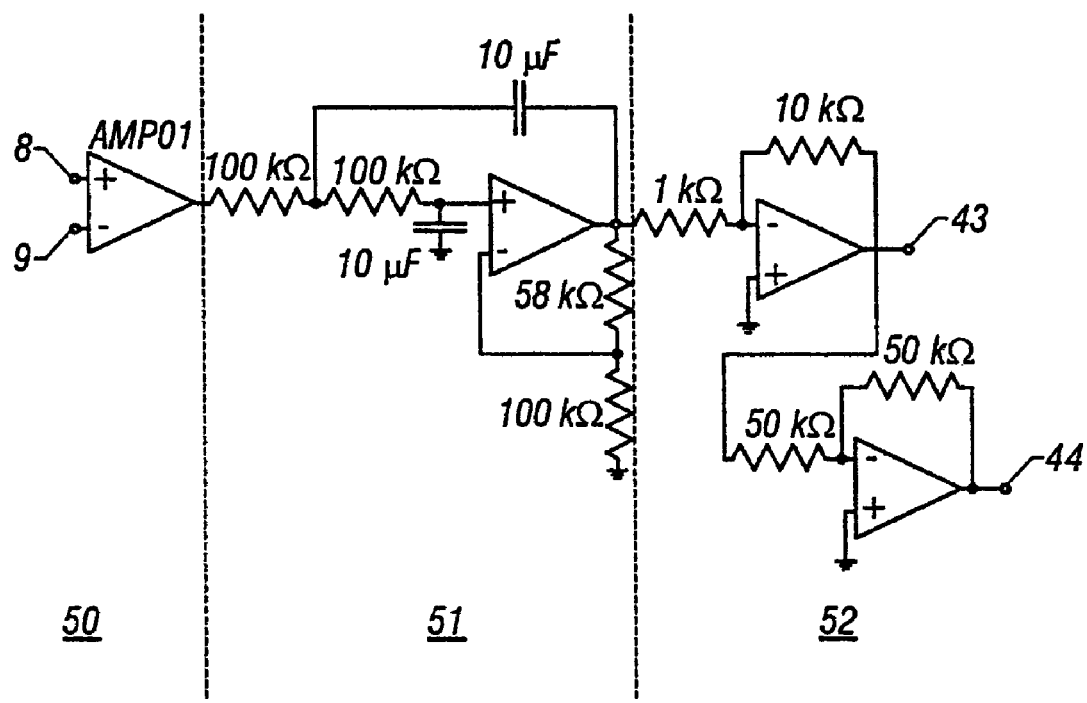
FIG. 5 shows a feedback alignment circuit of the invention.

An example of a feed back circuit useful for altering the position of an optical component is shown in FIG. 5. As set forth above, a differential amplifier 50 produces a signal having a sign and amplitude that correlates with the position of a radiation beam. The signal is passed through a low-pass filter 51 having a corner frequency of 0.16 Hz to the piezo-mounted mirror feedback 52 which includes a first 43 and second 44 piezoelectric controller. Piezoelectric controllers 43 and 44 power piezo electric elements 45 and 46, respectively as described above. The piezoelectric controllers are controlled via a 0 to 10 volt input signal. Thus, the amplitude and sign of the signal from the differential amplifier controls the movement of the piezo-mounted mirror 20, thereby altering the position of the radiation beam to align it with reflective surfaces 10 and 11.

Figure 2:
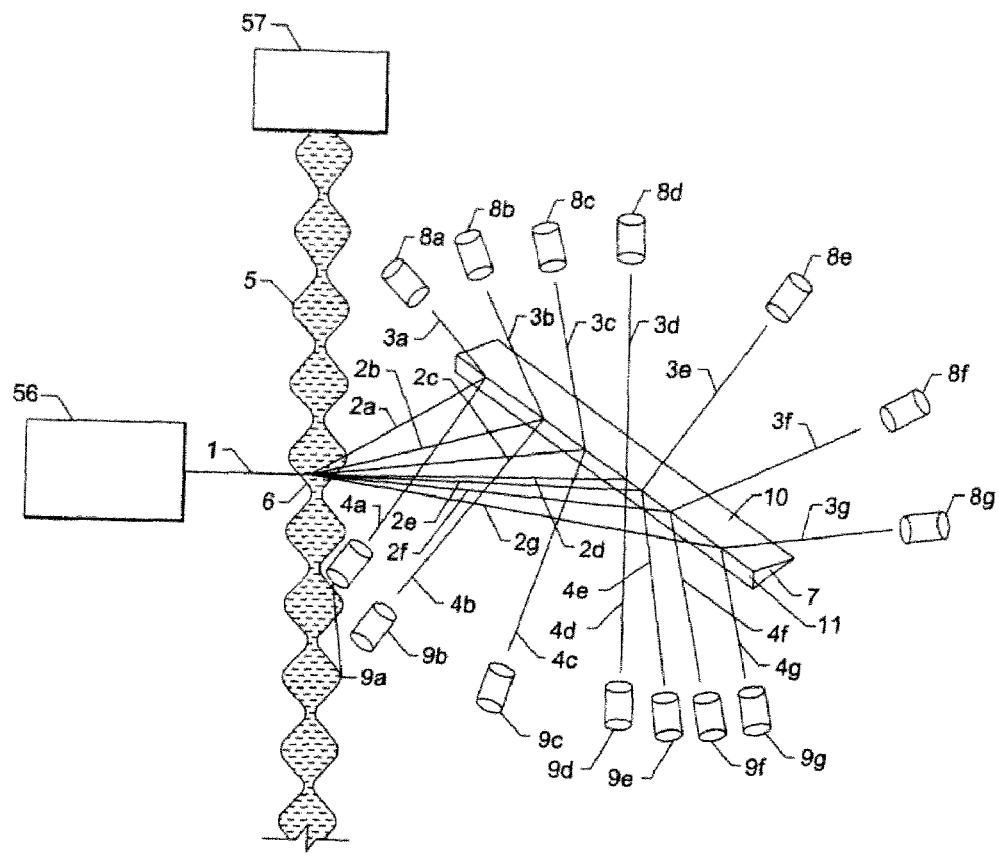
FIG. 2 shows a photodiode difference detector having a plurality photodiode detectors.

A difference detector of the invention can contain a first set of detectors placed to selectively detect radiation directed from a point, such as a location in a fluid stream, to different locations on a first reflective surface of a wedge. The difference detector can further include a second set of detectors placed to selectively detect radiation directed from the point to different locations on the second reflective surface. An example of a difference detector having a first and second set of detectors is shown in FIG. 2. A reflective wedge is formed by elongated reflective surfaces 10 and 11. Reflective surfaces 10 and 11 form a 90 degree angle between each other. A radiation beam 1, from a radiation source 56, contacts a particle 6 in a fluid stream 5 exiting from an optionally positionally adjustable nozzle 57 and radiation is scattered by particle 6. Scattered radiation is shown 20 as beams 2a through 2c and 2e through 2g in FIG. 2 along with direct radiation beam 2d. Scattered radiation that contacts surface 10 is reflected to detectors 8a through 8c and 8e through 8g, the paths of which are shown by beams 3a through 3c and 3e through 3g. Similarly, scattered radiation that contacts surface 11 is reflected in the opposite direction to detectors 9a through 9c and 9e through 9g, the paths of which are shown by beams 4a though 4c and 4e though 4g. The direct beams can be detected with detectors 8d and 9d as described above with regard to FIG. 1. As shown in FIG. 2 detectors in set 8 and set 9 can be placed in two arcs such that the lines of sight from the detectors to the wedge are coplanar.

A difference detector of the invention having plurality of detectors to selectively detect radiation directed from different locations on the reflective surface of a wedge can be used to determine the location of a radiation beam in a full range of directions covering two-dimensions. The location of a radiation beam can be determined in one dimension, the up and down direction, using the orientation shown in FIG. 2, according to the difference in output of detectors 8*d* and 9*d*. Similarly, the output of the first set of detectors 8*a* through 8*g* can be compared with the output of the second set of detectors 9*a* through 9*g* to determine the position of beam 1 in the first dimension (up and down) because radiation will be scattered equally in all directions when centered on fluid stream 5. Thus, if beam 1 is centered on reflective surfaces 10 and 11, the amount of radiation directed to the first set of detectors 8 is equivalent to the amount of radiation directed to the second set of detectors 9 and the detectors are balanced with a difference output of 0 volts. Changes in the position of beam 2 in the up and down direction can be detected according to the amplitude and sign of the difference output of detector set 8 and detector set 9.

The location of radiation beam 1 in the side-to-side direction can be determined by comparing the output of a first detector that is directed to a point on surface 10 that is on one side of direct beam 2*d* (for example, detector 8*a*) to the output of a second detector that is directed to a point on surface 10 that is on the other side of direct beam 2*d* (for example, detector 8*g*). The side-to-side location of the beam can be determined from the difference output of detectors on either side of the direct beam because radiation will be scattered equally in all directions from fluid stream 5. Similarly, the outputs of a first pair of detectors from opposite sets that detect points on the same side of direct beam 2*d* (for example, detectors 8*a* and 9*a*) can be compared to the outputs of a second pair of detectors from opposite sets that detect points on the other side of direct beam 2*d* (for example, detectors 8*g* and 9*g*). By measuring differences in the outputs of detectors across two sets of orthogonal directions, up/down and side/side, as described above, the location of a radiation beam in two dimensions can be determined.

Although 7 detectors are shown in each set of FIG. 2, totaling 14 detectors, it is understood that fewer detectors can be used. For example, difference detection can be achieved with 4 detectors, 2 in each set, that are symmetrically placed for a balanced output when a beam is centered in both the up/down direction and side to side directions shown in FIG. 2. Four detectors that are placed with such symmetry in FIG. 2 are 8*a*, 8*g*, 9*a* and 9*g*. Although beam position can be determined with sufficient accuracy for a number of applications of the invention using 2 detectors in each set, the number of detectors can be increased to increase the accuracy of position determination or alignment as desired for a particular application. Thus, each set of detectors can include 4, 5, 6, 8, 9, 10, 15, 20 or more detectors.

Accordingly, the invention provides a method for determining the relative position of a radiation beam that contacts a fluid stream. The method includes the steps of (a) directing a radiation beam from a radiation source to a fluid stream, thereby producing scattered radiation; (b) contacting the scattered radiation with the reflective exterior of a wedge formed by a first reflective surface and a second reflective surface, the first and second reflective surfaces placed to reflect radiation scattered in different directions from the fluid stream to different detectors, and (c) selectively detecting radiation reflected to the different detectors, wherein the relative amount of radiation intensity reflected to each of the different detectors correlates with the position of the radiation beam.

Figure 3:
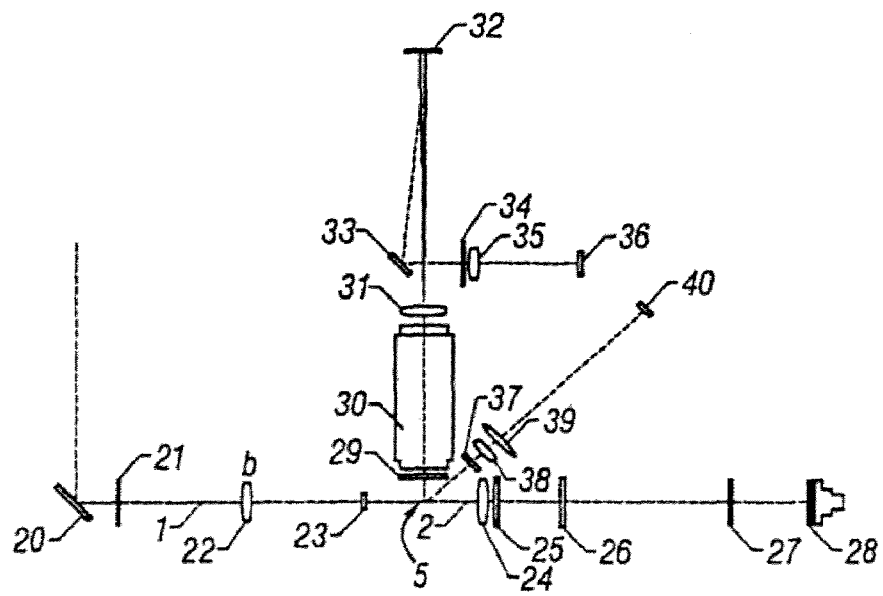
FIG. 3 shows the optical pathway of a flow sorter of the invention.

A difference detector of the invention can be used in a flow cytometer or flow sorter. An exemplary configuration of a flow cytometer including a difference detector of the invention is shown in FIG. 3. Those skilled in the art will recognize from the exemplary configuration shown in FIG. 3 and the description provided herein regarding difference detectors of the invention and their use, that a difference detector can be placed in a flow cytometer using a variety of configurations and components. Thus, a flow cytometer can be modified after manufacture to include a difference detector or can be designed and built to include a difference detector.

FIG. 3 shows an optical path for a flow cytometer in which a radiation beam produced by a single argon ion laser (Innova 300, Coherent, Santa Clara, Calif.) at 488 nm, with an output power of 40 mW can be directed to piezo mirror 20 which can be placed to reflect an incident radiation beam from the laser through an iris diaphragm 21 to lens 22. An iris diaphragm can be used to align a radiation beam and can be adjusted to have different size apertures for passage of beams having different cross sectional shapes or diameters. An iris diaphragm useful in the invention can include, for example, diaphragm SM1D12 from Thorlabs, Newton, N.J. Lens 22 (f=75 mm) can be placed to focus the radiation beam to a 20 micrometer spot when it contacts a fluid stream 5 after passing through a window 23. Scattered radiation can be directed from fluid stream 5 by one or more lens including, for example, lens 53 and lens 55, thereby being directed to the reflective surfaces forming the wedge of difference detector 26. Scattered and direct laser radiation that misses the reflective surface of the wedge is detected by forward scatter optics 28 after passing an iris diaphragm 27.

A flow cytometer of the invention can include a drop camera 40 placed to observe the vicinity of the drop break-off point of fluid stream 5 as shown in FIG. 3. A drop camera can be used to monitor qualities of the stream or drops including, for example, trajectory, drop size, break-off point, or drop interval. An illumination diode can be included to facilitate observation of the stream or drops. The illumination diode can be chosen to project light of any desired wavelength. Preferably the wavelength will be longer than that detected by emission and scatter detectors to avoid interference with sample detection. A lens 38 can be placed between a flow chamber containing fluid stream 5 and drop camera 40 to project an image of the drops or drop break-off point, onto the sensitive area of camera 40. Additionally, a filter 39 can be placed in front of drop camera 40 in order to block excitation radiation while passing radiation from the illumination diode. In one embodiment, the illumination diode can illuminate in the IR region and filter 39 can be a long pass filter with a cut on wavelength that is below the IR illumination produced by the diode and above the highest excitation wavelength contacting the sample stream. Placement of window 37 in the path from the flow chamber to drop camera 40 can seal the flow chamber while allowing light from the illumination diode to reach drop camera 40.

As shown in FIG. 3, emission from fluid stream 5 and an image of fluid stream 5 can pass through a scatter bar 29 that is positioned to block excitation radiation that is reflected off the surface of the jet. Emitted radiation can be collected by a lens 30 and collated by a lens 31 such that two or more radiation beams can be directed to pin hole mirror 32. Proper alignment of the optical components will allow a radiation beam to pass through a pin hole in screen 32 to contact a detector. A pinhole mirror can have one or more pinholes. As shown in FIG. 3, two properly aligned excitation radiation beams can pass through two pin holes. Thus, a pinhole mirror can have at least two pinholes, at least three pinholes or any number of pinholes desired to accommodate the number of radiation beams or detectors used in a particular application of the invention. The mirrored surface prevents passage of misaligned radiation, can be used to determine the trajectory or focus of a misaligned radiation beam and can be used to observe an image of the fluid stream 5.

A camera 36 can be placed to observe the surface of pinhole mirror 32 for determining alignment of the fluidic and optical paths of a flow cytometer. As shown in FIG. 3, an image of a misaligned radiation beam and sample stream can be reflected to camera 36 by a help mirror 33. A help mirror 33 can be included to reflect an image from screen 32 away from an emission radiation beam path so that a detection camera does not interfere with the emission beam. A lens 35 can be placed to focus an image reflected from screen 32 to camera 36. Additionally, a filter 34 can be placed to block excitation radiation beams from reaching camera 36.

The invention further provides a method for aligning a radiation beam with a fluid stream. The method includes the steps of (a) directing a radiation beam from a radiation source to a fluid stream, thereby producing scattered radiation; (b) contacting the scattered radiation with the reflective exterior of a wedge formed by a first reflective surface and a second reflective surface, the first and second reflective surfaces placed to reflect radiation scattered in different directions from the fluid stream to different detectors; (c) selectively detecting radiation reflected to the different detectors, wherein the relative amount of radiation intensity reflected to each of the different detectors correlates with the position of the radiation beam, and (d) adjusting the position of the radiation beam until a desired relative amount of radiation intensity is reflected to the detectors, thereby aligning the radiation source with the fluid stream.

As described above, a difference detector of the invention can be used to determine the position of a radiation beam that contacts a fluid stream based on the pattern of radiation scatter from a radiation beam that contacts the fluid stream. The output of the detectors can be compared in the vertical and horizontal directions and used to direct the positioning of a radiation beam. For example, differential amplifiers can be used to control the movements of positioning devices attached to a reflective surface such as a piezo-mounted mirror for automated alignment with a feedback circuit such as that shown in FIG. 5 and described above. Such a feedback circuit between a differential amplifier for vertical detectors and a piezo-mounted mirror can be used to automatically align a radiation beam in a vertical direction as described in Example I. As also described in Example I, piezo stacks can be placed to allow movement of the mirror in the horizontal direction. Using a feedback circuit for vertical control of mirror position in combination with a second similar feedback circuit between a differential amplifier for horizontal detectors and the horizontal piezo stacks of a piezo-mounted mirror, the position of the mirror can be rotated about an axis to change the position of a radiation beam in two dimensions.

A feedback circuit used to alter the position of a piezo-mounted mirror or other optical device can be directed by the difference output of any number of detectors depending upon the level of accuracy desired for a particular application of the invention, as described above. For example, a vertical or horizontal feedback circuit, or both, can compare the outputs of 2 or more detectors. Looking to FIG. 2 as an example, a vertical feedback circuit can be controlled by a differential amplifier that compares the outputs of the 7 detectors shown as 8a through 8g, observing one reflective surface of the wedge, to the outputs of the 7 detectors shown as 9a through 9g, observing the other reflective surface of the wedge. Similarly, a horizontal feedback circuit can be controlled by a differential amplifier that compares the outputs of the 6 detectors shown as 8a, 8b, 8c, 9a, 9b and 9c, observing points on one side of the direct beam, to the outputs of the 6 detectors shown as 8e, 8f, 8g, 9e, 9f and 9g, observing points on the other side of the direct beam. Any appropriately symmetric subset of these combinations can be compared by a differential amplifier controlling a feedback circuit, so long as the output of the combination correlates with the location of the radiation beam. Thus, a differential amplifier can compare the outputs of 4, 6, 8, 10, 12, 20, 30 or more detectors to control the position of a radiation beam.

The invention provides a method for determining the relative positions of a radiation beam, fluid stream and one or more particle detectors. The method includes the steps of (a) directing a radiation beam from a radiation source to a fluid stream, thereby producing scattered radiation; (b) contacting the scattered radiation with the reflective exterior of a wedge formed by a first reflective surface and a second reflective surface, the first and second reflective surfaces placed to reflect radiation scattered in different directions from the fluid stream to different alignment detectors; (c) selectively detecting radiation reflected to the different alignment detectors, wherein the relative amount of radiation intensity reflected to each of the different alignment detectors correlates with the positions of the radiation beam and the fluid stream, and (d) observing an image of the fluid stream on a pinhole mirror, wherein the pinhole mirror has at least one pinhole positioned to pass radiation from the fluid stream to at least one particle detector when the image of the fluid stream is at a desired position and when a desired relative amount of radiation intensity is reflected to each of the different alignment detectors.

The relative positions of a radiation beam, fluid stream and particle detector can be determined by determining the position of the radiation beam relative to the fluid stream and determining the position of the particle detector relative to the fluid stream. Thus, the fluid stream is used as a reference for aligning the three components. The position of the radiation beam relative to the fluid stream can be determined using a difference detector of the invention such as those shown in FIGS. 1 and 2 and described above. The position of the particle detector relative to the fluid stream can be determined using a pinhole mirror. An example of an apparatus having a difference detector and pinhole mirror that can be used for determining the relative positions of a radiation beam, fluid stream and particle detector is shown in FIG. 3.

The position of a fluid stream can be determined relative to a particle detector according to the position of its reflection on a pinhole mirror in which the pinholes are aligned with the particle detectors. A pinhole mirror can be placed such that radiation passing through one or more pinholes of the pinhole mirror is directed to one or more particle detectors. The image of a fluid stream or radiation emitted from the fluid stream on the pinhole mirror can be observed from a vantage for which the position or range of positions for the image is known when the fluid stream and the one or more particle detectors are aligned with each other. The image can be observed by eye or with an image detection device including, for example, a camera such as a charged coupled device camera, photographic camera or digital camera. Accordingly, based on the position of the image on the pinhole mirror, it can be determined whether or not the stream and particle detectors are aligned and, if they are not aligned, the direction of movement of the stream required to achieve alignment can be readily determined.

The invention further provides a method for aligning a radiation beam, fluid stream and one or more particle detectors. The method includes the steps of (a) directing a radiation beam from a radiation source to a fluid stream, thereby producing scattered radiation; (b) contacting the scattered radiation with the reflective exterior of a wedge formed by a first reflective surface and a second reflective surface, the first and second reflective surfaces placed to reflect radiation scattered in different directions from the fluid stream to different alignment detectors; (c) selectively detecting radiation reflected to the different alignment detectors, wherein the relative amount of radiation intensity reflected to each of the different alignment detectors correlates with the positions of the radiation beam and the fluid stream; (d) observing an image of the fluid stream on a pinhole mirror, wherein the pinhole mirror has at least one pinhole positioned to pass radiation from the fluid stream to at least one particle detector when the image of the fluid stream is at a desired position and when a desired relative amount of radiation intensity is reflected to each of the different alignment detectors, and (e) adjusting the relative positions of the radiation beam and the fluid stream until a desired relative amount of radiation intensity is reflected to the detectors and the image of the fluid stream is observed at the desired position, thereby aligning the radiation source, fluid stream and one or more particle detectors.

Methods for changing the position of a radiation beam are described above and in Example I. The methods can be used in combination with methods for changing the position of a fluid stream in order to align a radiation beam, fluid stream and one or more particle detectors. Although alignment by changing the position of the radiation beam or fluid stream or both are described herein to exemplify the methods, it is understood that the invention can be used to achieve similar alignment by altering the position of the particle detector, pinhole mirror or difference detector or a combination of these components.

A fluid stream can be produced by applying pressure to a liquid and causing it to pass through the discharge opening of a nozzle. A stream emerging from a discharge opening of a nozzle can be directed in a vertical downward direction to cross an observation zone where the fluid stream is intersected by a horizontal radiation beam path. Particles individually entering the zone of detection can be individually identified according to one or more responses to the radiation beam including, for example, absorption of radiation, emission of fluorescence, or scatter of radiation as detected by one or more particle detectors. Scattered radiation that leaves the observation zone can contact the reflective surface of a wedge in a difference detector.

The position of the fluid stream can be changed by altering the position of a nozzle through which it passes. A nozzle can be moved in a variety of directions to achieve alignment including, for example, translation in horizontal or vertical directions, or rotation that adjusts pitch or yaw angles along the vertical axis. The invention can be used to guide movement of the nozzle in a horizontal path orthogonal to the horizontal path of the radiation beam in order to alter the location of a sample stream until the excitation radiation beam and sample stream coincide for accurate detection. The invention can also be used to guide adjustment of the angle of the discharge opening of a nozzle relative to the orientation of the frame upon which it is supported such that a discharged fluid stream can flow vertically when the frame is placed upon an uneven or sloped surface. The invention provides vertical adjustment to raise or lower the discharge opening of a nozzle relative to a horizontal radiation beam path, thereby altering the location along a discharged fluid stream at which radiation is contacted. Such an alteration can allow convenient adjustment of the detection point relative to the drop break-off point. The nozzle can be attached to a positioning device that is manually adjusted or that receives controlling signals from an automated system such as a feedback circuit or computer controlled feedback algorithm.

A radiation beam and fluid stream can be aligned by iteratively detecting the position of the radiation beam using a difference detector or the position of the fluid stream using a pinhole mirror and adjusting the radiation beam or fluid stream until a desired alignment is achieved. The alignment methods can be performed manually or by an automated system. An automated system can include a computer processor that receives signals from a difference detector and imaging device directed to a pinhole mirror. The computer processor can receive instructions from an algorithm that include the alignment steps set forth above. The instructions can be written in any of the computer language that are known in the art.

An example of an automated system that can be adapted for aligning a radiation beam and fluid stream according to the invention is an autocentering algorithm. Autocentering algorithms are known in the art and are commonly used in microscopes to determine the location of a specimen on a microscope stage and to move the stage such that the specimen is properly aligned with an objective lens for observation. Similarly, an autocentering algorithm can be used to adjust the position of a fluid stream based on the location of an image on a pinhole mirror and the position of a radiation beam based on the output of a difference detector.

The invention provides a method for monitoring drop formation in an oscillating fluid stream, wherein drops separate from the oscillating fluid stream at a drop break-off point that is in phase with upstream drop boundaries. The method includes the steps of (a) directing a radiation beam to contact an oscillating fluid stream at an observation point, thereby producing scattered radiation; (b) detecting a change in the scattered radiation, wherein the change correlates with a drop boundary at the observation point in the oscillating fluid stream; (c) locating the drop break-off point in the oscillating fluid stream; (d) determining the phase between the drop boundary at the observation point and the drop break-off point, and (e) identifying from the phase the number of drops that will occur before the drop boundary reaches the drop break-off point.

When a fluid stream is formed at the opening of a nozzle, it forms a long cylinder. This cylinder is unstable and eventually breaks up into smaller drops. The fluidics of flow sorters have been designed to produce fluid streams with laminar flow. In most flow cytometers the nozzle has been designed with a Reynolds number (Re) of around 800, well within the Re<2300 regime needed for laminar flow in a tube. For laminar flow in a tube, the velocity profile is parabolic, with zero flow at the edges of the pipe. The average velocity is ½ of the maximum velocity at the center of the pipe. For a fluid stream in-air, the velocity profile is uniform across the width of the stream. As the velocity profile relaxes from the parabolic profile in the nozzle to the uniform profile in the stream, the diameter of the jet decreases. If the parabolic profile has fully developed, the diameter contracts to 0.866 times the nozzle diameter. In most cell sorters, the short nozzle orifice does not allow for a fully developed parabolic velocity profile in the nozzle, and the contraction of the stream is less than if the profile were fully developed as described in Pinkel & Stovel, "Flow Chambers and Sample Handling" in *Flow Cytometry: Instrumentation and Data Analysis*, London, Academic Press, pp 77-128 (1985).

A cylinder of water in air that is formed by a nozzle is unstable and the breaking up of the cylinder in to smaller drops is energetically favored. For a jet of water in air, disturbances with wavelengths greater than the circumference of the jet can be induced at the nozzle and will grow along the length of the jet. Disturbances with a wavelength less than the diameter of the jet are attenuated by the effects of surface tension and die out. Because both viscosity and surface tension depend on temperature, the break-off point can change if the temperature of the sheath fluid changes during a sort.

The initial disturbance can be provided by a piezoelectric element attached to the nozzle that produces acoustic waves that are coupled into the stream. A nozzle of the invention can vibrate with a flat frequency spectrum which can be tuned to match the speed and diameter of a fluid jet emitted from the nozzle. The frequency at which the nozzle oscillates can be controlled by application of an alternating voltage. Examples of oscillators useful for causing a vibration in a nozzle of the invention include a piezoelectric element or electromagnetic transducer. One skilled in the art will be able to determine appropriate oscillation frequency to achieve desired droplet interval, size or distance from discharge opening according to the relationships described below.

For disturbances with $\lambda > \pi d_{jet}$, the disturbances grow exponentially with time. The amplitude of a periodic disturbance (a) is given by $$a(t) = a_0 e^{\gamma t} \quad \text{(Eq. 2)}$$

where $a_0$, is the amplitude of the surface disturbance at the opening of the nozzle and $\gamma$ is the exponential growth rate, and depends on the wavelength ($\lambda$) of the disturbance and the viscosity and surface tension of the fluid. $\gamma$ has a maximal value at $\lambda_{max} = 4.508 \, d_{jet}$, where $d_{jet}$ is the diameter of the jet, and decreases with increasing wavelength beyond this point. No growth is possible for disturbances with wavelengths below $\pi d_{jet}$. The time at which the disturbance grows to ½ of the jet diameter and drops break off from the stream is then given by $$t_{break\text{-}off} = \frac{1}{\gamma} \ln\left(\frac{d_{jet}}{2a_0}\right) \quad \text{(Eq. 3)}$$

The radius of the jet as a function of distance from the nozzle (x) and of time (t) is given by $$r_{jet}(x, t) = r_{ave} + a_0 e^{\left(\gamma \frac{x}{v_{jet}}\right)} \cos\left(\omega t - \omega \frac{x}{v_{jet}}\right) \quad \text{(Eq. 4)}$$

where $r_{ave} = d_{jet}/2$, $v_{jet}$ is the velocity of the jet and $\omega$ is the angular frequency of the surface disturbance (see, for example, Main, *Vibrations and Waves in Physics*, Cambridge University Press, Cambridge (1993)). At the break-off point $$x_{break\text{-}off} = \frac{v_{jet}}{\gamma} \ln\left(\frac{d_{jet}}{2a_0}\right). \quad \text{(Eq. 5)}$$

The periodic disturbance will equal ½ of the jet diameter when $$\cos\left(\omega t - \omega \frac{x_{break\text{-}off}}{v_{jet}}\right) = -1, \text{ or } \left(\omega t - \omega \frac{x_{break\text{-}off}}{v_{jet}}\right) = \pi + n2\pi \quad \text{(Eq. 6)}$$

where n is an integer.

The methods of the invention for monitoring periodic disturbances in a fluid stream provide the advantage of predicting the location of the drop break-off point as the number of drops that will break from the stream between the time a drop boundary is observed and the time it reaches the drop-break off point and forms a drop. Thus, the methods can be used to replace distance measurements with an integer value that accurately predicts when a particular drop will break from the stream. This digital measure of the distance allows for more accurate calibration and sorting in a flow cytometer than is provided when distances are measured as length because the digital measure provides whole numbers with discreet solutions as opposed to distances which must be infinitely divided to approach the accuracy of a discreet value. Furthermore, the methods of the invention can be used to observe and account for every drop that breaks from a fluid stream, whereas methods which rely on video images to monitor drop formation are limited by the camera speed. In many cases cameras having speeds of 60 frames/sec are used to observe a stream that breaks at a rate of 100 drops/sec, thereby being incapable of observing all drops that break from the stream.

As set forth above, a difference detector of the invention can be used to observe patterns of radiation scatter from a fluid stream that has been contacted with a radiation beam. As demonstrated in Example II, a difference detector of the invention can be used to monitor oscillations in a fluid stream. Drop boundaries that form in an oscillating fluid stream as regions of narrowed diameter can be observed as changes in the amplitude of a difference detector of the invention. The results of Example II further demonstrate that the changes in the output of a difference detector of the invention correlate with oscillations in the stream. Thus, a method for monitoring drop formation can include contacting the scattered radiation from an oscillating fluid stream with the reflective exterior of a wedge of a difference detector of the invention and detecting a change in the amount of radiation reflected from a surface of the wedge. Radiation reflected to the different detectors can be selectively detected under conditions where the relative amount of radiation intensity reflected to each of the different detectors correlates with the position of the radiation beam. Oscillations in the fluid stream can be monitored with 2 or more detectors. As set forth above, a difference detector can include a first and second set of detectors placed to selectively detect radiation directed from the fluid stream to different locations on the first and second reflective surfaces, respectively.

The invention provides a method for sorting drops by monitoring drop formation according to the methods described above and isolating one or more of the drops from other drops that break off from the oscillating fluid stream. Because a difference detector of the invention can accurately measure changes in an oscillating fluid stream, the quality and consistency of the properties of the fluid stream can be monitored by the difference detector. As demonstrated in Example II, aberrations in the properties of the fluid stream including for example, changes in frequency or amplitude of surface oscillations, can be detected in response to physical perturbation of a flow cytometer such as a sharp tap, changes in the content of fluid stream such as passage of different sized particles or alteration in the oscillations of the nozzle such as perturbation of the piezo signal driving the oscillations of the nozzle. The difference detector can be used to detect a short term disturbance such as that induced by the passage of a large particle through the fluid stream or a long term disturbance such as ringing that results from altering the piezo signal to the nozzle.

The methods of the invention for monitoring an oscillating fluid stream can be used as a basis for determining when to stop or start a sorting procedure. For example, when aberration is observed in the difference detector signal, sorting can be stopped until the fluid stream returns to a normal oscillation pattern at which time sorting can be resumed. The methods can be carried out by an individual operating an instrument or alternatively by an automated system. The automated system can include a computer capable of receiving signals from the difference detector and having instructions for evaluating the signals received from the difference detector. The instructions for evaluating the signals received from the difference detector can include instructions to decide if the oscillations in the signal are out of a predefined frequency or amplitude range indicative of normal behavior then to send a signal to the sorter to stop sorting. The instructions can further be capable of deciding if the oscillations in the signal are within a predefined frequency or amplitude range indicative of normal behavior then to send a signal to the sorter to start sorting.

A method of monitoring oscillation in a fluid stream can be carried out by digitizing and storing the photodiode output over a period of time such as the last 100 cycles of photodiode difference detector output. For each time point, for example, every 1/16th cycle, the current value can be compared to the average value over the last 100 cycles for that time point. If the current value is within a predetermined window around the average value for the time point, sorting is allowed to continue uninterrupted. The current time point can be compared to an average value in order to detect sudden changes in break off point. To detect slow changes over time, a maximum and minimum value for the photodiode difference amplitude can be set. If a detected value does not fall within the desired range, sorting is not allowed.

A method of monitoring drop formation can further include a step of observing the drop break-off point with a camera. An example of an apparatus of the invention that includes a drop camera is shown in FIG. 3 and described above. A drop camera can be used to measure the distance between the drop break-off point of a fluid stream and a point upstream such as an observation point or the location of the nozzle tip. Based on this distance and the oscillations of the fluid stream the phase between an observed drop boundary and the drop break-off point can be determined. The method can further include a step of illuminating the vicinity of the drop break-off point with pulsed radiation. The use of pulsed or strobed illumination provides the advantage of facilitating observation of the drop break-off point and increasing accuracy of distance measurements based on location of the drop break-off point.

The drop break-off point can also be observed by irradiating the path of the fluid below the drop break off point with a radiation beam and detecting a change in radiation passing through the drop break-off point. The rate at which the drops break off can be determined as the rate at which radiation-scattering liquid drops pass through the beam, so long as the diameter of the radiation beam is narrower than the space between the drops. The location of the drop break-off point can also be determined by detecting radiation passing through the drop break-off point produced by a radiation beam that is narrower than the space between the liquid drops. The location of the drop break-off point can be determined as the furthest upstream point in the stream where intersection with the beam causes alternating beam scatter and transmittance, due to alternating passage of drops punctuated by gaps between the drops. The phase between an observed drop boundary and the drop break-off point can be determined from the location of the drop break-off point, as described above.

The invention further provides a method for assigning a particle in an oscillating fluid stream to a drop that breaks off of the oscillating fluid stream. The method includes the steps of (a) directing a radiation beam to contact an oscillating fluid stream at an observation point, thereby producing scattered radiation; (b) detecting a change in the scattered radiation, wherein the change correlates with a drop boundary at the observation point; (c) detecting a particle that is adjacent to the drop boundary in the oscillating fluid stream; (d) locating the drop break-off point in the oscillating fluid stream; (e) determining the phase between the drop boundary at the observation point and the drop break-off point, and (f) identifying from the phase the number of drops that will break off of the oscillating fluid stream before the drop boundary reaches the drop break-off point, thereby assigning the particle that is adjacent to the drop boundary in the oscillating fluid stream to a drop.

A sample containing particles to be sorted can be injected into the center of a sheath fluid stream, upstream of the measurement or laser crossing point using methods well known in the art. Prior to measurement, the channel through which the fluid stream passes can be narrowed, thereby stretching and accelerating the stream. Because of this hydrodynamic focusing, the sample stream in the core of the sheath fluid narrows, providing precise placement of the particles. Stable laminar flow can be maintained allowing the sample stream to remain narrow and centered in the core of the sheath-fluid stream at the illumination point.

A particle can be identified in a fluid stream according to one or more measured parameters. The measured value of each parameter can be compared to a set range for that parameter. If a cell meets the-desired criteria, it is selected to be sorted. Sorting can be achieved for a fluid stream that passes two plates with a potential difference of several thousand volts and located below the drop break-off point. The sheath fluid can consist of a conductive liquid such as a solution of 0.9% saline. Just before the drop containing the selected cell breaks off from the jet, the stream is charged, and then grounded after the drop breaks off. The drop that was to be sorted maintains an electrical charge as it breaks off from the jet, and all other drops are left uncharged. The charged drop is deflected by the electrical field between the plates and collected. The uncharged drops fall directly into a drain. The selected cells can be bulk sorted into a single collection vessel, or index sorted one at a time into individual wells, such as in a 96-well plate.

A particle in a sample stream that passes through a radiation beam intersection point can be characterized by a variety of criteria including, for example forward scatter, perpendicular scatter, or fluorescence as described, for example, in Shapiro supra (1995). For a single radiation beam, a number of different measurements can be made including, for example, forward scatter, perpendicular scatter, and three or four colors of fluorescence measurements. Additional lasers can be used, increasing the number of fluorescence wavelengths measured. When more than one radiation beam is used, each can be focused on the stream in a separate location. As a particle passes through each beam, the signals measured can be delayed an appropriate amount to allow all the signals to be attributed to the same event.

Thus, the invention provides a method for sorting drops. The method includes monitoring drop formation according to the methods described above and further includes a step of isolating the drop containing a particle of interest from other drops that break off from the oscillating fluid stream. Because the invention allows drop formation to be monitored according to the number of drops, rather than based on distance alone, the invention can provide an increase in sort rate and efficiency of sorting. In particular, the size of a coincidence rejection window can be reduced. The coincidence rejection window is the amount of time allowed for a particle to clear the break-off point. Most flow sorters use coincidence rejection windows spanning three or more drops to accommodate errors in the ability to predict drop location. The present invention provides the advantage of identifying discreet drops, thereby allowing coincidence rejection windows to be less than three drops. Thus, the coincidence rejection window can be adjusted to depend on the position of a single drop or particle.

The following examples are intended to illustrate but not limit the present invention.

Example I

Automated Alignment of Flow Cytometer Fluidics and Optics

This example describes an apparatus for determining the relative positions of a laser beam and fluid stream based on the position of scattered light produced by the laser beam at the point of contact with the fluid stream. This example further describes an apparatus and automated method for aligning the laser and fluid stream.

The apparatus used consisted of a standard flow cytometry system having a number of modifications and custom parts as described in Asbury et al., *Cytometry* 40:80-101 (2000) and Asbury et al., *Cytometry* 24:234-242 (1996). The flow cytometer was further modified to include a piezo-mounted mirror that allowed for precise movements of the laser spot, and a photodiode difference detector as described below.

The piezoelectric mounted mirror was placed in the optical path of the excitation laser beam such that it could be used to direct the beam to a fluid stream. The piezo mounted mirror is shown in FIG. 4. A one inch mirror (02-MPG-007; Melles Griot, Irvine, Calif.) was mounted, using a UV-polymerizable glue, on four piezoelectric stacks (AE0203D08; Thorlabs, Newton, N.J.) placed 90 degrees apart around the rim of the mirror. The piezoelectric elements were fixed to a 1 inch glass disk that was mounted in an adjustable optical mounting. The piezoelectric elements were powered by piezoelectric controllers (MDT690; Thorlabs, Newton, N.J.) that produced voltages from 0 to 100 volts. The piezoelectric elements were operated in pairs, one pair aligned horizontally, and the other pair aligned vertically such that changes in the length of the piezo stacks caused the mirror to rotate. The full angular mirror displacement from each pair of piezoelectric elements was 0.014 inch, independent of the other pair. The piezoelectric controllers were controlled via a 0 to 10 volt input signal. The 0.014 inch angular deflection resulted in a 50 micrometer displacement of the laser spot at the particle stream.

The flow cytometer further included a photodiode difference detector. Two 1/10 inch thick glass microscope slides were ground to a 45 degree angle at one end and cut to 0.59 inch in length. Both the angled and flat ends of the slide were polished on a lapping wheel using a series of diamond grit wheels. A housing was machined that held the slides with a 1/4 inch diameter photodiode (A-453; Melles Griot, Irvine, Calif.) mounted to the flat end of each slide as shown in FIG. 1. The slides were placed to abut each other as shown in FIG. 1 to form a wedge having reflective surfaces. Radiation from the laser is reflected into the slides at the wedge, and the position or movements of the laser can be determined from the difference in the photodiode outputs.

The housing was mounted on a 3-axis positioner in line with the forward scatter detector, directly in front of the scatter bar. The laser light was incident to the smooth surface of the glass, with the ground groove in the back. Laser light that hit the angled slide ends was reflected upward or downward in the plane of the glass. Scattered and direct laser light that missed the ground wedge passed through the glass slide and was detected by the forward scatter optics. The photodiodes received direct laser light that reflected off of the groove in the back surface of the glass slide. A differential amplifier (AMP-01; Analog Devices, Norwood, Mass.) was used to compare the outputs of the two photodiodes. The differential gain of the amplifier was set to 1000×. For the signal used during alignment and feedback to the piezo-mirror, a low-pass filter with a corner frequency of 0.16 Hz was used. The amplifier, filter, and feedback circuits are shown in FIG. 5.

The optical and fluidic components were mounted on an air supported optical air table. A single argon ion laser (Innova 300, Coherent, Santa Clara, Calif.) was used, at 488 nm, with an output power of 40 mW. Saline solution (9 g/L) was used for sheath fluid. A 70 micrometer nozzle produced a stream approximately 63 micrometers in diameter, and a 12 psi sheath fluid pressure was used unless indicated otherwise. Within the fluid stream, the particle stream was centrally located and was about 15 micrometers in diameter. Unless indicated otherwise samples consisted of calibration beads having an average diameter of 1 micrometer (Polysciences, Warrington, Pa.). The beads emitted fluorescence with a peak value at 540 nm when excited with the 488 nm laser.

Radiation from the laser was directed, using a series of tilted mirrors, so that the laser was axially aligned with the focusing lens and the forward scatter optics. A lens (f=75 mm) focused the laser down to a 20 micrometer spot at the laser crossing point of the fluid stream. Radiation from the irradiated fluid stream was collected by a microscope objective (M Plan Apo 20, Mitutoyo, Japan) and focused onto a custom fabricated pinhole mirror. The pinhole acted as a spatial filter for light passing through it as described in Asbury et al., supra (2000). Light that passed through the pinhole was filtered (488RB, Chroma Technology) to remove laser light, and the fluorescent signal was collected by a photomultiplier tube (PMT) (H957-06; Hamamatsu, Bridgewater, N.J.). A CCD camera ("pinhole camera") imaged the light reflected off of the pinhole mirror, and displayed the image on a video monitor. The video monitor provided a visual indication of the alignment of the stream, laser, and collection optics. FIG. 3 shows the optical pathway in the sorter. The flow sorter electronics are described in van den Engh et al., *Cytometry* 10:282-293 (1989).

DC Alignment of the Laser and Photodiode Difference Detector

Measurement of photodiode difference detector outputs to determine position of the laser beam were made first with no fluid stream in place, and then repeated with the fluid stream in place. No differences in the ability to determine position of the laser beam were noted when the fluid stream was properly aligned with the laser compared to when the fluid stream was absent.

Figure 6:
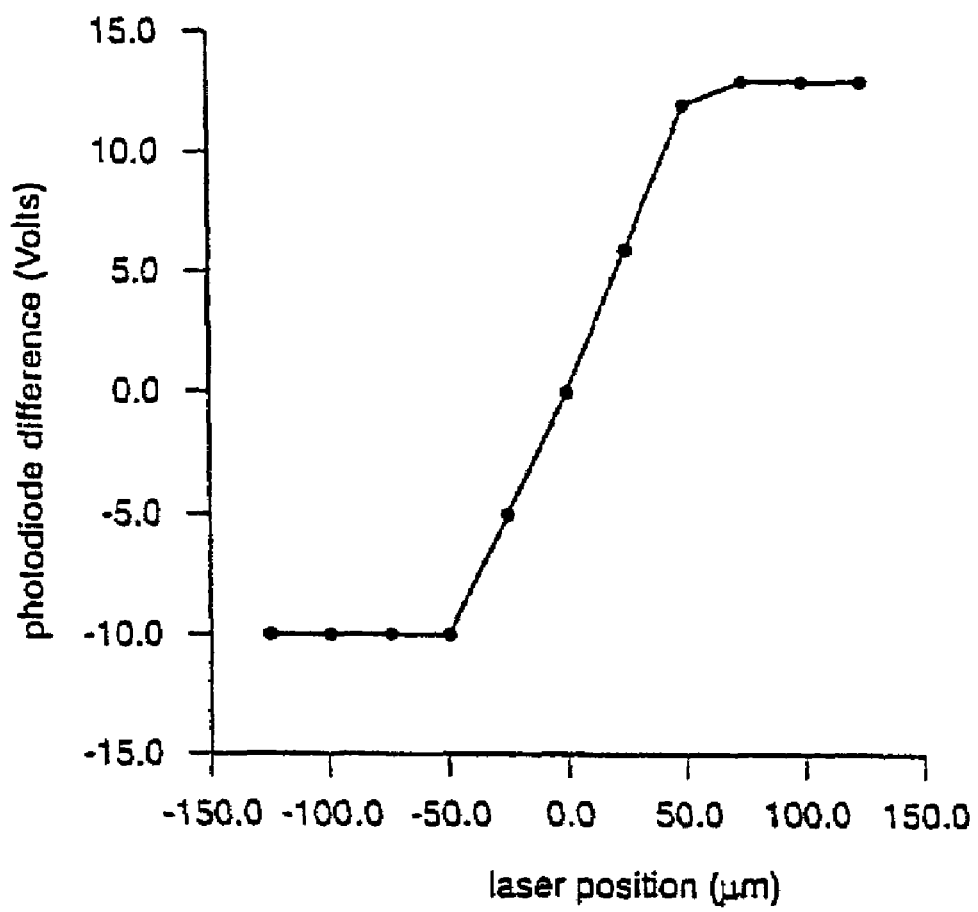
FIG. 6 shows the output of a photodiode difference detector of the invention as a laser-spot is translated along the Z axis of a fluid stream using a laser focusing lens.

The position of the laser spot was translated up and down along the Z-axis (which runs parallel to the direction of the fluid stream) by moving the laser focusing lens. As shown in FIG. 6, the output of the photodiode difference amplifier responded in an approximately linear manner to changes in position of the laser spot with a slope of 0.22 volt/micrometer. The slight difference of the slope in the up and down directions, and the difference in maximum photodiode difference amplitude is likely due to manufacturing inconsistencies between the upper and lower glass slides. Such inconsistencies can be avoided by machining the slides, rather than grinding and polishing them by hand.

The laser spot was moved up and down along the Z-axis by tilting the piezo-mounted mirror. The photodiode difference detector response to movements of the piezo-mounted mirror was similar to that seen when the laser focusing lens was used to move the laser spot. As is commonly seen with piezoelectric actuators, some hysteresis in the angle of the mirror occurred. Despite the slight hysteresis, the range of the piezo elements from positive 100 to negative 100 volts corresponded well with the dynamic range of the photodiode detector running from positive 10 to negative 10 volts. Comparison of the results from the tilting of the piezo-mounted mirror with those from the translation of the laser focusing lens indicated that the response of the piezo mounted mirror was 0.5 micrometer of laser-spot displacement per volt of piezo control signal.

Piezo Feedback

Figure 7:
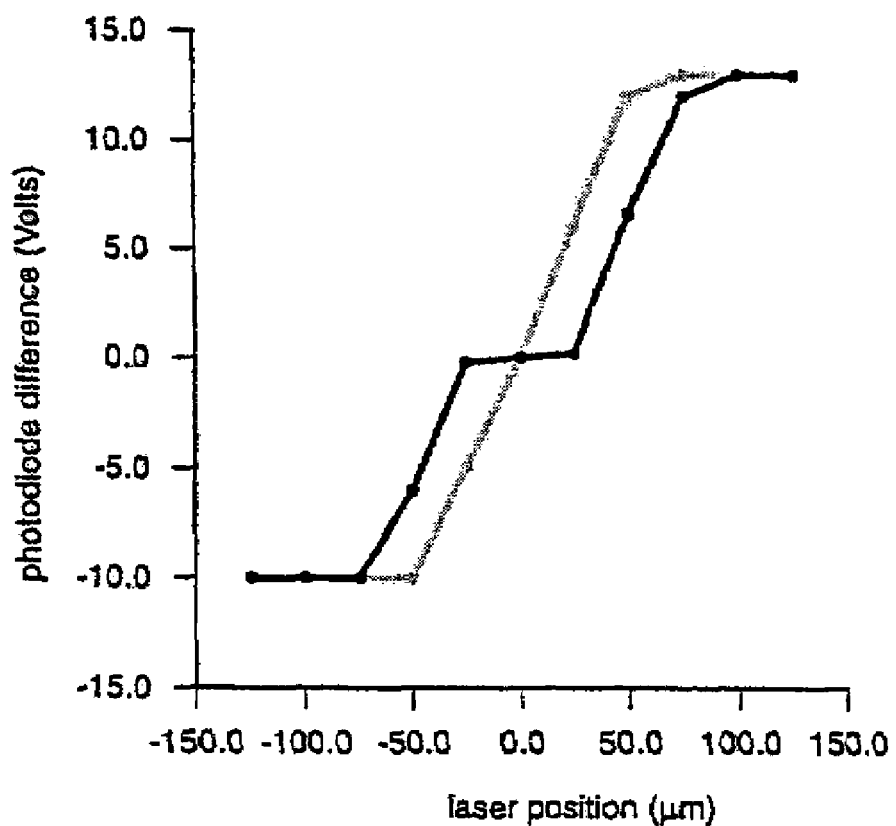
FIG. 7 shows piezo feedback control of laser position as a laser-spot is translated along the Z axis of a fluid stream using feedback control (black) overlayed with laser position as the laser-spot is translated along a similar path with no feedback control (grey).

The output of the photodiode difference amplifier was used to correct for misalignment of the laser. Drift of the laser was simulated by moving the laser focusing lens in the Z-direction. To achieve feedback control, the output of the photodiode difference amplifier was used to control the voltages to the piezo-mounted mirror thereby automatically tilting the mirror in response to the simulated drift. FIG. 7 shows the output of the photodiode difference amplifier as the laser-spot was translated along the Z axis under feedback control (black line) overlayed with the output of the photodiode difference amplifier as the laser-spot was translated along the Z axis absent feedback control (grey line). As demonstrated by the results of FIG. 7, the feedback control system was able to maintain a photodiode difference output of about 0 in response to perturbations in the position of the radiation beam that caused the radiation spot to move 25 micrometers either side of center. Thus, the feedback control system was able to automatically re-align the beam with the difference detector for misaligning perturbations of the radiation beam spot spanning a range of 50 micrometers.

The range of movement of the piezo element can be modified by using elements with different physical properties, for example, longer or shorter elements. Alternatively precision motors for small mechanical displacements that can be obtained from a number of optical supply companies such as New Focus, Ealing, ThorLabs, and Applied Precision, can be used.

Horizontal Alignment of the Laser and Particle Stream

Figure 8:
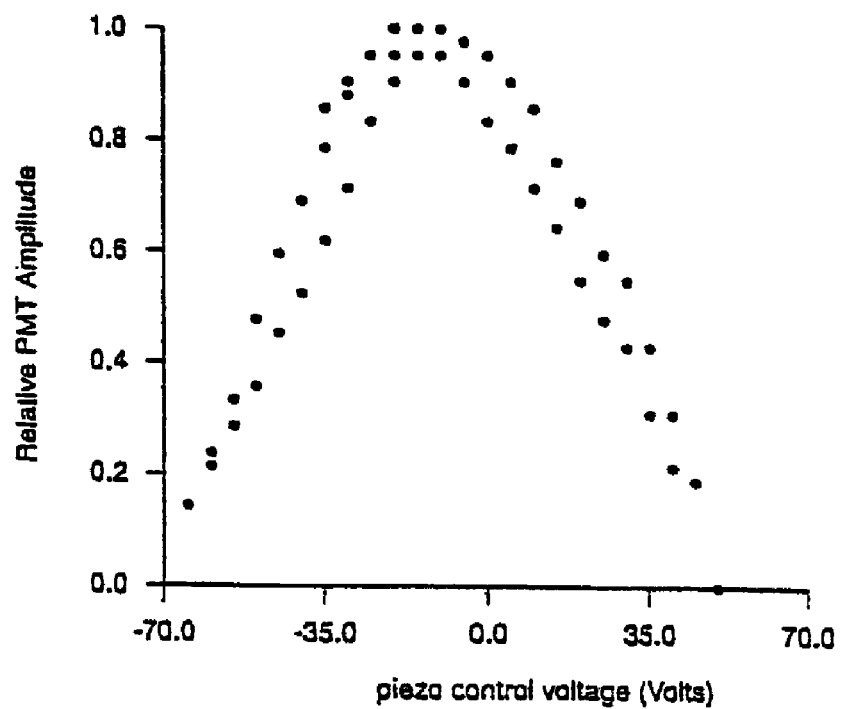
FIG. 8 shows relative fluorescent intensity vs. piezo control voltage when a piezo mirror is moved to direct a laser beam to different locations along the diameter of a fluid stream.

By adjusting the piezo voltage to the horizontal piezo stacks on the piezo-mounted mirror, the laser spot was moved horizontally in the Y-direction (orthogonal to the direction of flow of the fluid stream). FIG. 8 shows fluorescence measurements from 1 micrometer calibration beads as the piezo mirror was used to move the laser spot across the diameter of the fluid stream. As shown in FIG. 8, maximum fluorescence intensity was measured at a position of the mirror corresponding to a piezo control voltage of about −10 to −20 volts. The results of FIG. 8 indicate that the piezo mounted mirror can be adjusted and the shape and amplitude of the fluorescent signed observed to align the laser and the particle stream.

Example II

Drop Boundary Detection in a Flow Sorter

This example demonstrates detection of oscillations in a fluid stream using a photodiode difference detector. This example further demonstrates determination of the frequency of drop formation and location of a drop break-off point based on the output of a photodiode difference detector.

Figure 9:
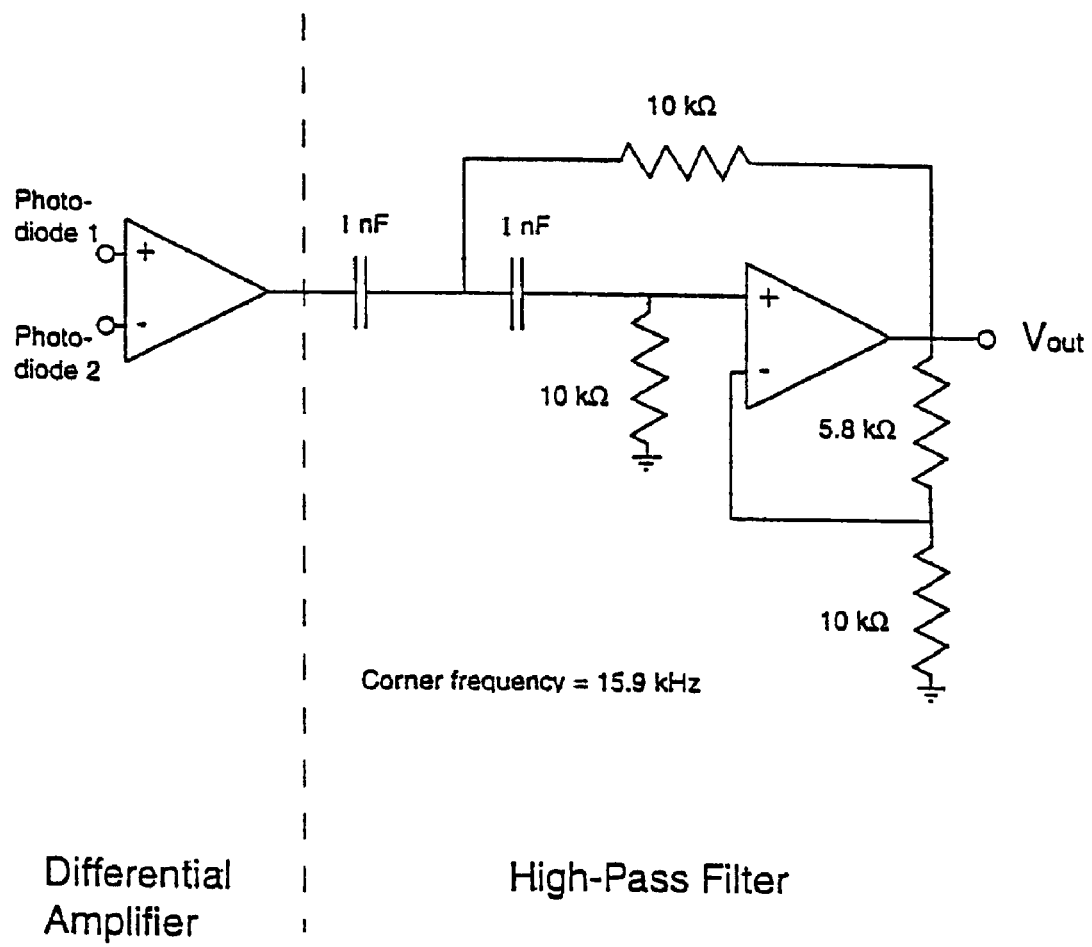
FIG. 9 shows a circuit used for drop-boundary detection.

The results described in this example were obtained using the flow cytometry setup described in Example I. The signal from the photodiode difference detector was filtered by a 15 kHz high-pass filter to remove noise. The circuit diagram for the amplifier and filter used is given in FIG. 9. In order to determine the effect of large particles on the formation of drops, 25 micrometer beads (18241, Polysciences, Warrington, Pa.) were used as test particles.

Drop Boundary Formation

Figure 10:
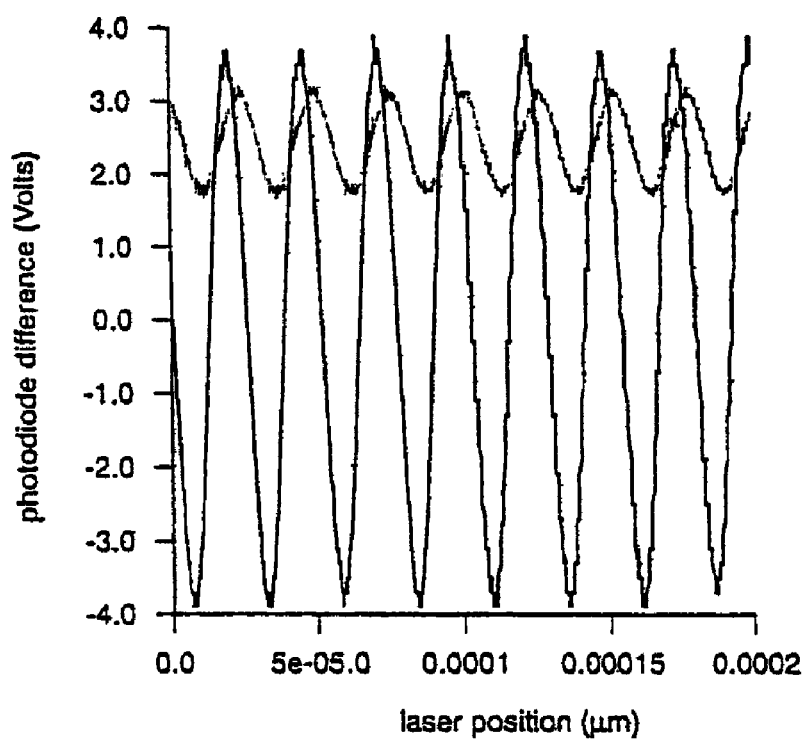
FIG. 10 shows the piezo drive waveform (gray) and the output of the photodiode difference amplifier (black) at a piezo drive frequency of 28 kHz. The piezo drive waveform is that applied to a piezoelectric annulus that is mounted to a nozzle through which the fluid stream has been evacuated. The photodiode difference detector amplitude is measured at the intersection of the fluid stream and a laser beam downstream of the nozzle.

A piezoelectric annulus mounted to the nozzle of the flow cytometer was used to induce oscillations of the fluid stream evacuating the nozzle. As a result, ripples were formed on the surface of the fluid stream. These ripples were detected at the laser crossing point as oscillations in the radiation passing through the stream. FIG. 10 shows the piezo drive waveform that was used to provide a stable drop break-off point (grey) in the oscillating fluid stream overlayed with the photodiode difference signal (black) detected at the crossing point of the radiation beam and oscillating fluid stream. The measurement was made with 12 psi of sheath fluid pressure and a piezo frequency of 28 kHz. The results of FIG. 10 indicate that the oscillation measured by the photodiode difference detector corresponded to the frequency of the crystal drive voltage for the case of a simple sine wave.

The amplitude of the photodiode difference detector varied with the presence of air bubbles or clogs in the nozzle. For a given sheath fluid pressure and piezo drive voltage, the piezo drive frequency that resulted in the maximum amplitude of the photodiode difference detector signal also gave the shortest fluid stream length when drop formation was observed.

Figure 11:
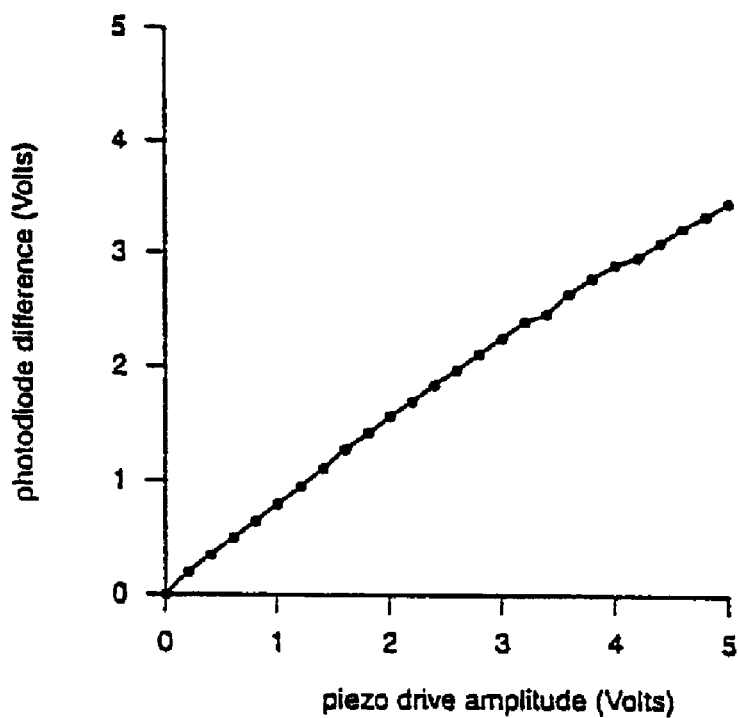
FIG. 11 shows photodiode difference detector amplitude vs. piezo drive signal amplitude for radiation passing through an oscillating fluid stream.

The amplitude of the photodiode difference detector was measured as a function of the piezo drive amplitude. While the frequency of the piezo drive voltage was kept constant at 39 kHz with a sheath fluid pressure of 12 psi, the amplitude of the piezo drive was increased from zero up to the limits of the piezo drive signal generator. As shown in FIG. 11, the amplitude of the photodiode difference detector output was found to increase as the amplitude of the piezo drive was increased. These results demonstrated that the photodiode difference detector can be used to monitor changes in the oscillation of the fluid stream.

Phase and Velocity of Drop Boundaries

The phase of the photodiode difference detector signal relative to the piezo drive signal was found to depend on the distance between the nozzle and the laser-crossing point, the frequency of the piezo drive signal and the velocity of the stream. When the height of the nozzle was varied so that the phase between the photodiode difference detector signal and the piezo drive signal changed by 360 degrees, the wavelength ($\lambda$) of the disturbance in the fluid stream was determined. From the wavelength and the frequency of the photodiode difference signal, the velocity of the fluid stream was determined. The velocity of the fluid stream as determined by this method was compared to the velocity of the fluid stream calculated using Equation 1:

$$V_{jet} = \sqrt{2P/\rho} \qquad \text{(Eq. 1)}$$

where P is the pressure of the fluid stream across the nozzle opening and ρ, the density of the fluid, was set at 0.998 g/cm³ (the density of water at 20 degrees). For all measurements, the measured velocity was about 20% less than the theoretical value. This lower velocity was most likely due to pressure losses in the tubing resulting in the pressure at the nozzle being lower than the pressure indicated by the gauge. Volume collection measurements over time gave fluid stream velocity values in the same range as those determined from the wavelength and the frequency of the photodiode difference signal. These results demonstrated that the photodiode difference detector can be used to determine the velocity of an oscillating fluid stream.

Alignment of Laser, Fluid Stream, and Detector

The ability to detect the ripples on the surface of the fluid stream depended on the proper alignment of the laser, fluid stream, and detector. As set forth in Example I and demonstrated by the results of FIG. 6, the alignment of the laser and the detector in the Z-direction affected the DC output of the photodiode difference detector. If the addition of the ripple signal to the DC photodiode difference voltage did not extend beyond the dynamic range (+/−10 volts) of the detector, the high frequency measurements of the fluid stream ripple were not affected by the alignment of the laser and detector in the Z-direction. This dynamic range was not limited by the photodiode difference amplifier circuit which had a dynamic range of +/−15 volts.

Figure 17:
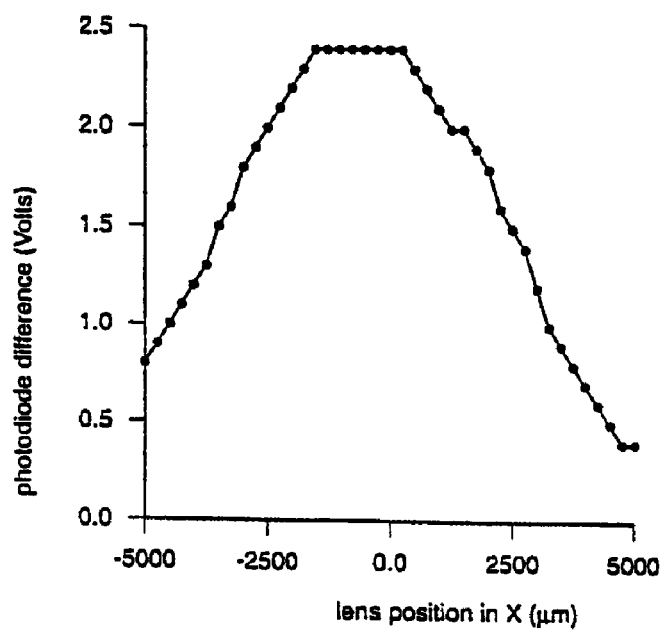
FIG. 17 shows photodiode difference amplitude as a function of laser focusing lens position along an axis orthogonal to the direction of a fluid stream.

As shown in FIG. 17, proper focusing of the laser at the laser-fluid stream crossing point provided maximal photodiode difference signals from the photodiode difference detector. The width of the laser focusing that provided the maximal photodiode difference detector output was 1750 micrometers. These results demonstrated that the amplitude of the detector signal was sensitive to the focusing of the laser, and was able to provide diagnostic information regarding cytometer alignment similar to that obtained using the methods described above for detecting fluorescent peaks from beads (see also FIG. 8).

Frequency Response

Figure 12:
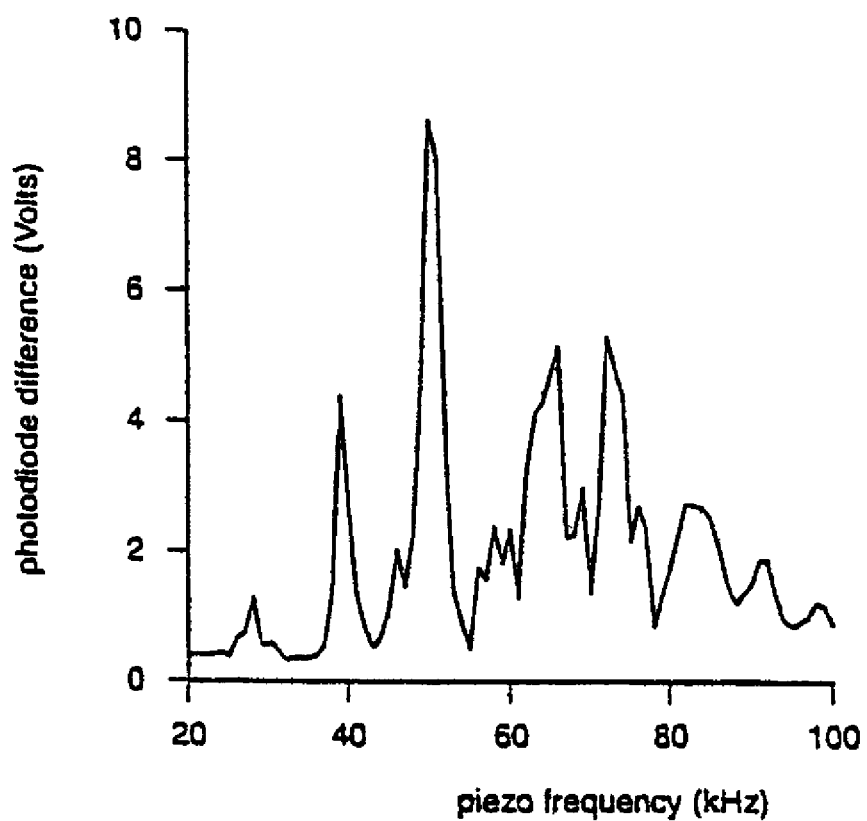
FIG. 12 shows photodiode difference amplitude measured for radiation passing through an oscillating fluid stream as a function of the frequency of a piezoelectric annulus mounted to a nozzle through which the stream is evacuated.
Figure 13:
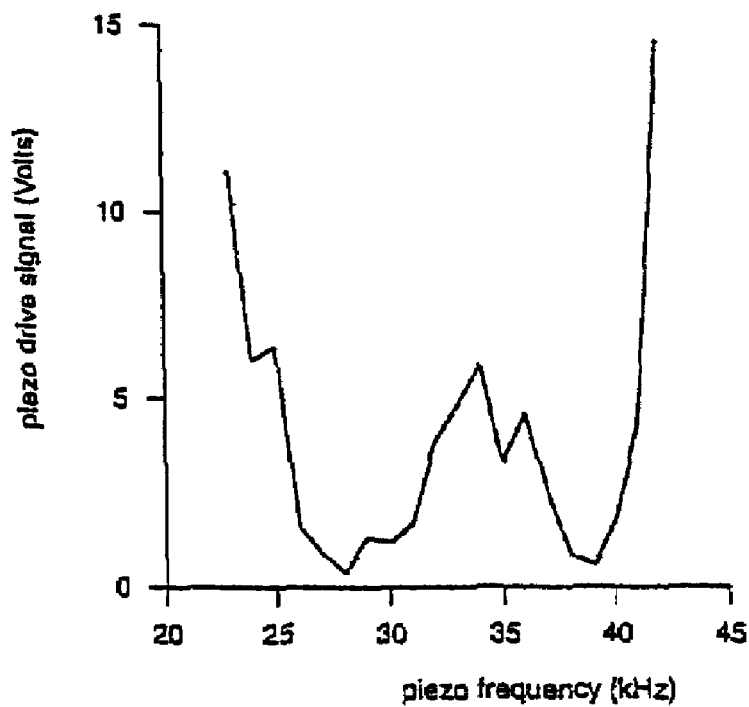
FIG. 13 shows the piezo drive voltage required to maintain a constant drop break-off point as the piezo drive frequency is varied.

The dependency of both drop formation and acoustic propagation within the nozzle were found to be dependent on the piezo drive frequency. FIG. 12 shows the amplitude of the photodiode difference output over a piezo drive frequency range of 20 to 100 kHz with a constant piezo drive voltage of 2.4 volts peak-to-peak and a sheath fluid pressure of 12 psi. At a sheath fluid pressure of 12 psi, and a nozzle diameter of 70 micrometers, drop formation was expected at frequencies below 43 kHz, with optimal drop formation at 28 kHz. The two peaks in the photodiode difference signal below 43 kHz, at 28 kHz and 39 kHz, corresponded to the two highest drop formation points observed. Drop formation is theoretically possible at frequencies lower than 20 kHz, but the drop formation point was lower than the range of the drop-camera so no measurements were made at piezo drive frequencies below 20 kHz.

Next, the piezo drive signal was varied in the range from 20 kHz to 45 kHz, where drop formation was observed, and the piezo drive voltage was adjusted to maintain a constant drop formation point. Measurement of the output of the photodiode difference detector at different piezo drive signal values in this range indicated that the minimum amplitude of the output of the photodiode difference detector was at 28 kHz. This value correlated with the theoretical optimal frequency for drop formation with the current setup.

FIG. 12 shows the piezo drive voltage required to maintain a steady drop break-off point as the piezo drive frequency was varied. The two minima at 28 kHz and 39 kHz corresponded to the peaks in the photodiode difference output in FIG. 12.

Relationship Between Piezo Drive Signal, Fluid Stream Disturbance, Drop Break-Off Point and Difference Detector Output In order to determine the relationship between break-off point and difference detector output, the break-off point and difference detector output were recorded as the piezo signal was varied. A sheath fluid pressure of 12 psi was used, which resulted in a fluid stream velocity of 9 m/s and a wavelength of 231 micrometers when driven at 39 kHz. The break-off point was measured using a drop camera to record the distance from the nozzle tip to the initial break-off point, and then a scale was placed on the monitor corresponding to the drop separation distance determined above. The laser-crossing point was 500 micrometers below the nozzle opening.

The distance between the drop break-off point and nozzle was measured as the piezo signal was varied. An exponential relationship was observed between break-off point and initial surface disturbance. The exponential relationship observed indicated that the relationship between piezo voltage and initial surface disturbance was linear as described, for example in van den Engh, "High speed cell sorting" *Emerging Tools for Single-Cell Analysis*, Wiley-Liss Inc., New York (2000). The extrapolated zero crossing point, where the initial disturbance is equal to ½ the fluid stream diameter, or 31.5 micrometers, was at a piezo voltage of 6154 volts. The relationship of initial surface disturbance to piezo signal is linear with a slope of 5 nanometers per volt. At the smallest piezo voltage observed, 0.11 volts, the calculated initial surface disturbance was 0.55 nm, enough to form stable drops. Table 1 gives the results of these measurements.

TABLE 1

| Piezo Drive voltage (volts) | Break-off point (micrometers) | detector output (volts) |
|---|---|---|
| 0.110 | 7493 | 0.270 |
| 0.153 | 7239 | 0.420 |
| 0.220 | 6985 | 0.580 |
| 0.306 | 6731 | 0.780 |
| 0.446 | 6477 | 1.130 |
| 0.651 | 6223 | 1.610 |
| 1.023 | 5969 | 2.460 |
| 1.456 | 5715 | 3.580 |

The exponential growth rate (γ) was determined using Equation 7.

$$\gamma = \frac{1}{t_{break\text{-}off}} \ln\left(\frac{d_{jet}}{2a_0}\right) \quad \text{(Eq. 7)}$$

Figure 14:
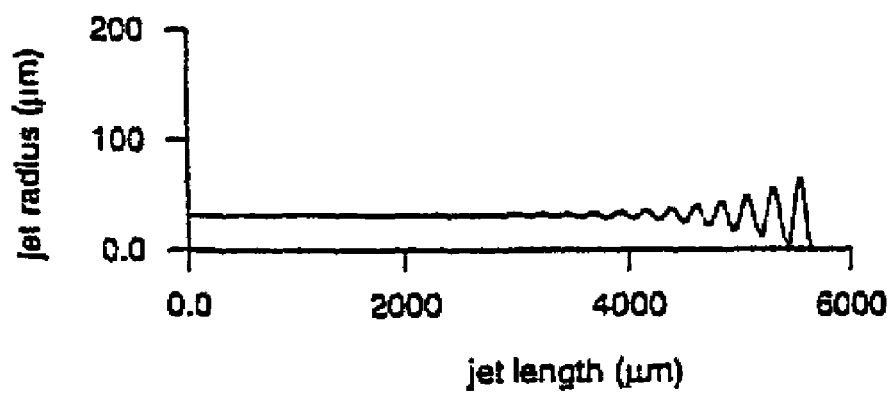
FIG. 14 shows simulation of fluid stream radius using Equation 6 as described in Example I, where average fluid stream radius was 31.5 micrometers, the initial surface disturbance was 0.01 micrometer, gamma was 13,192 $sec^{-1}$, the piezo drive frequency was 39 kHz, and the fluid stream velocity was 9 m/s.

For the case where the break off distance is 5715 micrometers, and the piezo voltage is 1.456 volts, the initial surface disturbance ($a_0$) was 7.25 nm and the break-off time, $t_{break\text{-}off}$ was 635 microsec. This gives γ=13010 sec⁻¹. FIG. 14 shows a simulation of fluid stream (jet) radius using Equation 6

$$\cos\left(\omega t - \omega \frac{x_{break\text{-}off}}{v_{jet}}\right) = -1 \quad \text{(Eq. 6)}$$

where $a_0$=10.0 nm, γ=13010 sec⁻¹, average fluid stream radius was 31.5 micrometers, the piezo drive frequency was 39 kHz and the fluid stream velocity ($v_{jet}$) was 9 m/sec. The simulation yielded a break off point of 5,635 micrometer which was similar to the empirically observed value.

Figure 18:
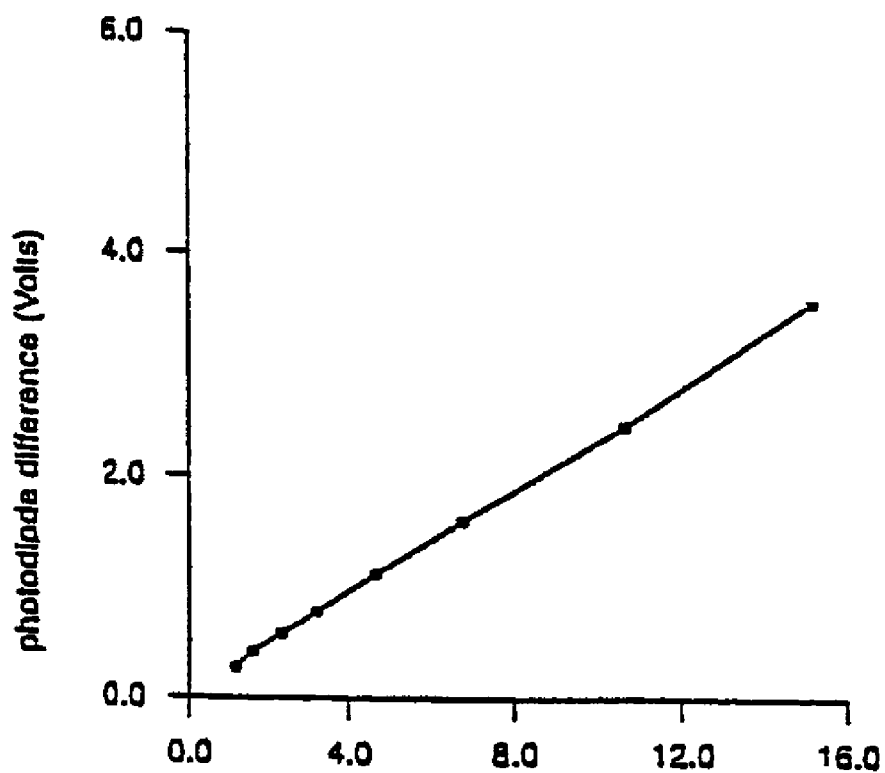
FIG. 18 shows photodiode difference amplitude versus the amplitude of the disturbance on the surface of a fluid stream at the laser crossing point.

FIG. 18 demonstrates the relationship between surface disturbance at the laser crossing and photodiode difference detector output. The relationship between surface displacement and photodiode difference detector output shown in FIG. 18 followed a similar exponential form to that observed between piezo voltage and photodiode difference detector output (Compare FIG. 11).

Based on the observed relationship between photodiode difference amplitude and break-off point and using values of $V_{piezo}=1.023$ volts and $d_{break-off}=5969$ micrometers (from Table 1), a change in break-off point of one drop separation distance was calculated to result in a −200 mvolt change in photodiode difference amplitude. Because the observed relationship between photodiode difference amplitude and break-off point was exponential, the photodiode difference amplitude was more sensitive to changes in break-off distance for break-off points that were closer to the nozzle tip. These results demonstrate that the output of the photodiode difference detector can be used to monitor the surface disturbance and thus the break-off point of the fluid stream in real-time.

Effects of Disturbances to the Piezo Signal on the Fluid Stream

In order to produce stable drop formation, simple-periodic signals can be used to vibrate the nozzle piezo. In order to investigate the sensitivity of the photodiode difference detector to transient disruptions of stable drop formation, the piezo drive signal was modified, and the resulting photodiode difference detector output recorded. A programmable function generator (33120A, Hewlett-Packard, Palo Alto, Calif.) was used, and the desired waveform points calculated.

Figure 15:
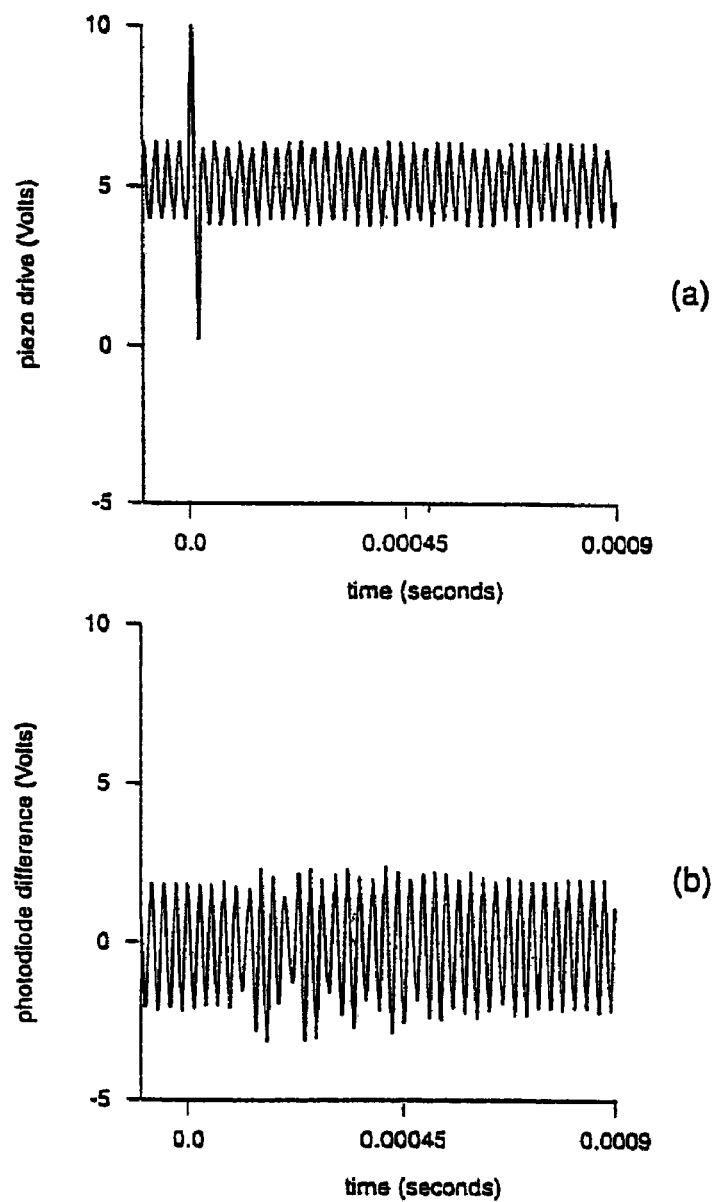
FIG. 15 shows the piezo voltage signal (a) with 99 cycles with amplitude of 2.5 volts and 1 cycle with amplitude of 10.0 volts, and the resulting photodiode difference signal (b).

A single peak with an amplitude of 10 volts was added to a train of 99 cycles with an amplitude of 2.5 volts as shown in FIG. 15A. The single 10 volt peak resulted in a ringing modulation in the photodiode difference detector output as shown in FIG. 15B. This ringing modulation was most likely due to the ringing of the piezo and its load. Determination of the envelope of the modulation indicated that the ringing had a frequency of 11.42 kHz, and demonstrated an exponential decay.

The photodiode difference detector output resulting from a sharp tap to the optical table was also determined. A plot of the photodiode difference signal with time showed that changes in the amplitude of the photodiode difference signal corresponded to fluctuations in the initial surface disturbances in the fluid stream. These disturbances led to variations in the break-off point that were significant enough to affect the ability to sort a desired particle.

Effects of Large Particles on the Fluid Stream

Figure 16:
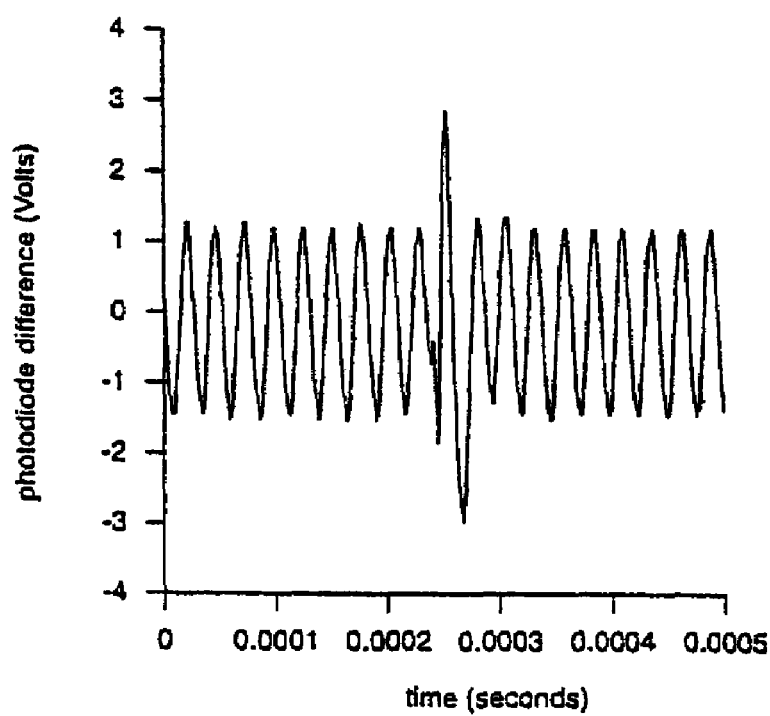
FIG. 16 shows output of the photodiode difference detector in response to the passage of a 25 micrometer bead through the nozzle.

Particles with a diameter of 25 micrometers (18241, Polysciences, Warrington, Pa.) were mixed 1:100 with standard 1 micrometer beads and the mixture was run in the flow cytometer at a rate of 3000 particles/second, which yielded, on average, 1 large bead every 1300 drops. FIG. 16 shows the photodiode difference signal resulting from the passage of a 25 micrometer bead. The largest recorded disruption of photodiode difference amplitude was 2 volts, which was calculated to cause a change in initial surface displacement from 7 nm to 17 nm. This change of 10 nm in initial surface disturbance corresponds to a change in break-off point from 5715 micrometers to 5108 micrometers.

This example demonstrates that the photodiode difference output had the same frequency as the piezo drive signal. The amplitude of the photodiode difference signal was exponentially related to the break-off distance, and linearly related to the amplitude of the surface disturbance of the fluid stream at the crossing point of the radiation beam and fluid stream. Thus, the output of the photodiode difference detector can be used to monitor drop boundaries based on reduced diameter in the oscillating stream. As demonstrated above, the output of the photodiode difference detector can also be used to determine the drop break-off point.

This example also demonstrates that the amplitude of the photodiode difference detector output was sensitive to the location within the fluid stream at which the laser beam crossed. These results indicate that the amplitude of the photodiode difference signal can be used to monitor alignment of the laser beam and fluid stream.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

What is claimed is:

1. An apparatus for determining the position of a radiation beam relative to a fluid stream, comprising:
   (a) a radiation source for producing said radiation beam;
   (b) an optionally positionally adjustable nozzle having a discharge opening, wherein said fluid stream exits through said discharge opening, said nozzle positioned to cause said fluid stream and said radiation beam to intersect;
   (c) one or more transparent members having a first reflective inner surface and a second reflective inner surface placed to reflect radiation scattered by said fluid stream, wherein said reflective inner surfaces are placed to form the reflective exterior of a wedge;
   (d) a first detector placed to selectively detect radiation reflected from said first reflective inner surface;
   (e) a second detector placed to selectively detect radiation reflected from said second reflective inner surface;
   (f) a differential amplifier, wherein said differential amplifier compares the intensity of radiation detected at said first and second detectors;
   (g) a third reflective surface placed to reflect radiation through said fluid stream;
   (h) a positioning device attached to said third reflective surface; and
   (i) a feed back circuit, wherein a signal from said amplifier directs said positioning device to change the position of said third reflective surface.

2. The apparatus of claim 1, wherein said transparent members comprise glass, plastic or quartz.

3. The apparatus of claim 1, wherein said transparent members are transparent to radiation in the UV, VIS, or IR regions.

4. The apparatus of claim 1, wherein said first and second detectors are attached to said one or more transparent members.

5. The apparatus of claim 1, wherein said reflective inner surfaces comprise mirrored surfaces.

6. The apparatus of claim 1, wherein said reflective inner surfaces are separated by an angle of 90° in said wedge.

7. The apparatus of claim 1, wherein said fluid stream is oscillating.

8. The apparatus of claim 7, wherein said fluid stream further comprises a particle of interest.

9. An apparatus for determining the position of a radiation beam relative to a fluid stream, comprising:
 (a) a radiation source for producing said radiation beam;
 (b) an optionally positionally adjustable nozzle having a discharge opening, wherein said fluid stream exits through said discharge opening, said nozzle positioned to cause said fluid stream and said radiation beam to intersect;
 (c) one or more transparent members having a first reflective inner surface and a second reflective inner surface placed to reflect radiation scattered by said fluid stream, wherein said reflective inner surfaces are placed to form the reflective exterior of a wedge;
 (d) a first set of detectors comprising detectors placed to selectively detect said scattered radiation from the intersection point between said radiation beam and said fluid stream to different locations on said first reflective inner surface;
 (e) a second set of detectors comprising detectors placed to selectively detect said scattered radiation from said intersection point to different locations on said second reflective inner surface;
 (f) a differential amplifier, wherein said differential amplifier compares the intensity of radiation detected at said first and second set of detectors;
 (g) a third reflective surface placed to reflect radiation through said fluid stream;
 (h) a positioning device attached to said third reflective surface; and
 (i) a feed back circuit, wherein a signal from said amplifier directs said positioning device to change the position of said third reflective surface.

10. The apparatus of claim 9, wherein the lines of sight from the detectors in said first set of detectors are coplanar.

11. The apparatus of claim 9, wherein the lines of sight from the detectors in said second set of detectors are coplanar with the lines of sight from the detectors in said first set of detectors.

12. The apparatus of claim 9, wherein said transparent members comprise glass, plastic or quartz.

13. The apparatus of claim 9, wherein said transparent members are transparent to radiation in the UV, VIS, or IR regions.

14. The apparatus of claim 9, wherein said first and second set of detectors are attached to said one or more transparent members.

15. The apparatus of claim 9, wherein said reflective inner surfaces comprise mirrored surfaces.

16. The apparatus of claim 9, wherein said reflective inner surfaces are separated by an angle of 90° in said wedge.

17. The apparatus of claim 9, wherein said fluid stream is oscillating.

18. The apparatus of claim 17, wherein said fluid stream further comprises a particle of interest.

19. An apparatus for determining the relative positions of a radiation beam, fluid stream and one or more particle detectors, comprising:
 (a) a radiation source for producing said radiation beam;
 (b) an optionally positionally adjustable nozzle having a discharge opening, wherein said fluid stream exits through said discharge opening, said nozzle positioned to cause said fluid stream and said radiation beam to intersect;
 (c) one or more transparent members having a first reflective inner surface and a second reflective inner surface placed to reflect radiation scattered by said fluid stream, wherein said reflective inner surfaces are placed to form the reflective exterior of a wedge;
 (d) a first set of alignment detectors comprising alignment detectors placed to selectively detect said scattered radiation from the intersection point between said radiation beam and said fluid stream to different locations on said first reflective inner surface;
 (e) a second set of alignment detectors comprising alignment detectors placed to selectively detect scattered radiation from said intersection point to different locations on said second reflective inner surface;
 (f) a differential amplifier, wherein said differential amplifier compares the intensity of radiation detected at said first and second alignment detectors;
 (g) a third reflective surface placed to reflect radiation through said fluid stream;
 (h) a positioning device attached to said third reflective surface;
 (i) a feed back circuit, wherein a signal from said amplifier directs said positioning device to change the position of said third reflective surface; and
 (j) a pinhole mirror, wherein said pinhole mirror has at least one pinhole positioned to pass radiation from said fluid stream to at least one particle detector.

20. The apparatus of claim 19, wherein the lines of sight from the alignment detectors in said first set of alignment detectors are coplanar.

21. The apparatus of claim 19, wherein the lines of sight from the alignment detectors in said second set of alignment detectors are coplanar with the lines of sight from the alignment detectors in said first set of alignment detectors.

22. The apparatus of claim 19, wherein said transparent members comprise glass, plastic or quartz.

23. The apparatus of claim 19, wherein said transparent members are transparent to radiation in the UV, VIS, or IR regions.

24. The apparatus of claim 19, wherein said first and second alignment detectors are attached to said one or more transparent members.

25. The apparatus of claim 19, wherein said reflective inner surfaces comprise mirrored surfaces.

26. The apparatus of claim 19, wherein said reflective inner surfaces are separated by an angle of 90° in said wedge.

27. The apparatus of claim 19, wherein said fluid stream is oscillating.

28. The apparatus of claim 27, wherein said fluid stream further comprises a particle of interest.

29. The apparatus of claim 28, further comprising a flow sorter positioned to isolate said particle of interest from said fluid stream.

30. The apparatus of claim 19, wherein said pinhole mirror has at least two pinholes.

31. The apparatus of claim 19, further comprising an image detection device placed to receive an image of said fluid stream on said pinhole mirror.

32. The apparatus of claim 31, further comprising a second mirror placed to reflect said image to said image detection device.

* * * * *